United States Patent [19]

Barth

[11] Patent Number: 4,591,459
[45] Date of Patent: May 27, 1986

[54] INTERMEDIATES FOR 6-(AMINOACYLOXYMETHYL) PENICILLANIC ACID 1,1-DIOXIDES

[75] Inventor: Wayne E. Barth, East Lyme, Conn.

[73] Assignee: Pfizer Inc., New York, N.Y.

[21] Appl. No.: 677,663

[22] Filed: Dec. 3, 1984

[51] Int. Cl.[4] .................. C07D 499/00; A61K 31/425
[52] U.S. Cl. ............................. 260/245.2 R; 514/196; 514/197; 424/114
[58] Field of Search ................. 260/245.2 R, 245.2 T; 514/196, 197

[56] References Cited

U.S. PATENT DOCUMENTS 4,287,181  9/1981  Kellogg ............................. 424/114
4,342,768  8/1982  Kellogg ............................. 424/250

FOREIGN PATENT DOCUMENTS 3302335  7/1983  Fed. Rep. of Germany .
2076812  12/1981  United Kingdom .

OTHER PUBLICATIONS

Greene, Protective Group in Organic Chemistry, p. 239 (1981).

Primary Examiner—Nicholas S. Rizzo
Attorney, Agent, or Firm—Charles J. Knuth; Albert E. Frost; Robert K. Blackwood

[57] ABSTRACT beta-Lactamase inhibitors which are aminoacid esters of 6-alpha- and 6-beta-(hydroxymethyl)pencillanic acid 1,1-dioxides; pharmaceutically-acceptable salts thereof; conventional esters thereof which are hydrolyzable in vivo; bis-methanediol esters thereof; or mixed methanediol esters with said beta-lactamase inhibitors and sulbactam. Pharmaceutical compositions comprising said beta-lactamase inhibitors and a conventional beta-lactam antibiotic, said compositions useful in the treatment of bacterial infections. Compounds useful as intermediates in the synthesis of said beta-lactamase inhibitors. Antibacterial mixed bis-methanediol esters of said aminoacyloxymethyl penicillanic acid 1,1-dioxides and ampicillin or amoxicillin, also useful in the treatment of bacterial infections; and intermediates therefor.

20 Claims, No Drawings

INTERMEDIATES FOR 6-(AMINOACYLOXYMETHYL) PENICILLANIC ACID 1,1-DIOXIDES

BACKGROUND OF THE INVENTION

The present invention relates to aminoacid esters of 6-alpha- and 6-beta-(hydroxymethyl)penicillanic acid 1,1-dioxides, pharmaceutically-acceptable salts thereof, conventional esters thereof which are hydrolyzable in vivo, bis-methanediol esters thereof; or mixed methanediol esters with said beta-lactamase inhibitors and sulbactam (penicillanic acid 1,1-dioxide), said methanediol esters also hydrolyzable in vivo. While some of these compounds possess antibacterial activity per se, their principal value is as beta-lactamase inhibitors. Thus they are useful in combination with conventional beta-lactam antibiotics (penicillins and cephalosporins) against microorganisms resistant or partially resistant to beta-lactam antibiotics through production of beta-lactamase enzymes. Also encompassed by the present invention are pharmaceutical compositions comprising a present beta-lactamase inhibiting compound and a conventional beta-lactam antibiotic; mixed bis-methanediol esters of the present beta-lactamase inhibiting compounds and a conventional beta-lactam antibiotic; pharmaceutical compositions of the latter mixed esters; methods of treating bacterial infections with either of the above pharmaceutical compositions; and compounds useful as intermediates in the preparation of these various compounds.

Related compounds, viz, penicillanic acid 1,1-dioxide and esters thereof readily hydrolyzable in vivo (Barth, U.S. Pat. No. 4,234,579); the bis-methanediol ester of sulbactam (Bigham, U.S. Pat. No. 4,309,347); various 6-alpha- and 6-beta-(hydroxymethyl)penicillanic acid 1,1-dioxides and esters thereof (Kellogg, European Patent Application No. 83,977; Kellogg, U.S. Pat. No. 4,287,181); and 6-alpha- and 6-beta-(aminoalkyl)penicillanic acid 1,1-dioxides (Barth, European Patent Application No. 84,925) have been previously described as beta-lactamase inhibitors useful in combination with beta-lactam antibiotics for the treatment of bacterial infections. Antibacterial bis-esters of methanediol with penicillins and penicillanic acid 1,1-dioxide (Bigham, U.S. Pat. No. 4,244,951; Godtfredsen et al., U.S. Pat. No. 4,342,772) have also been described. Talampicillin (USAN generic name), the 1H-isobenzofuran-3-on-1-yl ester of ampicillin, and (5-methyl-1,3-dioxol-3-on-4-yl)methyl ester of ampicillin (Sakamoto et al., U.S. Pat. No. 4,342,693) exemplify two in vivo hydrolyzable ester radicals of particular interest in the present case.

U.K. Patent Application No. 2,076,812 broadly discloses beta-lactamase inhibiting compounds of the formula

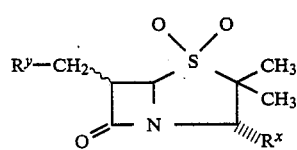

wherein $R^x$ is carboxy or protected carboxy, $R^y$ is hydroxy, etherified hydroxy ($R^zO-$) or esterified hydroxy (e.g., $R^zCOO-$), and $R^z$ is an optionally substituted hydrocarbon radical, thereby defining literally an infinite number of compounds. Since ethers wherein the group $R^z$ is a 1-aminoalkyl group are not formed by known methods, and would not be stable even if they could be formed, the definition of $R^z$ cannot be construed to include alkyl groups substituted in the 1-position with amino, alkylamino or dialkylamino groups.

SUMMARY OF THE INVENTION

The present invention relates to compounds of the formula

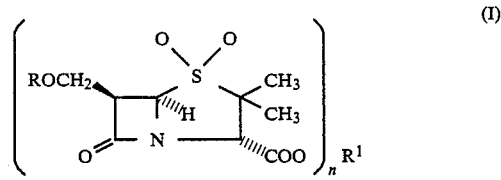

or

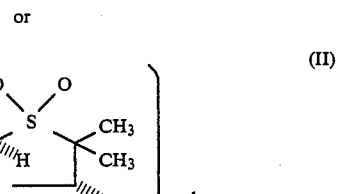

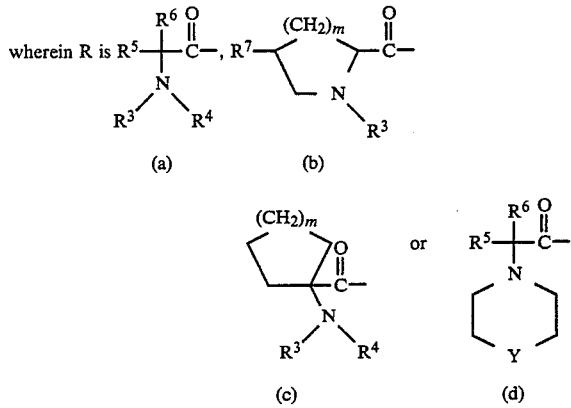

wherein R is

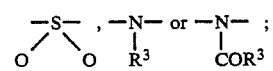

$R^3$, $R^4$ and $R^5$ are each independently hydrogen or $(C_1-C_3)$alkyl;
$R^6$ is hydrogen or optionally substituted $(C_1-C_6)$alkyl, phenyl or benzyl, wherein the optional substituent is $-OR^3$, $-SR^8$, $-SO_2R^8$, $-NR^3R^4$, $-NHCOR^3$, $-CONH_2$ or $-COOR^3$; with the proviso that when said substituent is $-COOH$, n is 1 and $R^1$ is hydrogen;
$R^7$ is hydrogen, hydroxy or $-OCOR^3$;
$R^8$ is $(C_1-C_3)$alkyl;
Y is $-(CH_2)_m-$, $-O-$, $-S-$, $$-\underset{\underset{O}{\overset{\displaystyle \|}{S}}\phantom{)}}{\overset{\displaystyle \|}{\underset{O}{\phantom{)}}}}-, -\underset{R^3}{\overset{\phantom{|}}{N}}- \text{ or } -\underset{COR^3}{\overset{\phantom{|}}{N}}-;$$

m is 0, 1 or 2; and
either
n is 1 and $R^1$ is hydrogen, a radical group forming an ester hydrolyzable under physiological conditions, or 1,1-dioxopenicillanoyloxymethyl; or
n is 2 and $R^1$ is $-CH_2-$;
a pharmaceutically-acceptable acid addition salt thereof; or a pharmaceutically-acceptable cationic salt thereof when n is 1 and $R^1$ is hydrogen.

It will be understood by those skilled in the art that when the group R contains an asymmetric carbon atom, each of the formulae (I) and (II) represent two different diastereoisomers (epimers). Depending on the stereochemistry, relative to natural amino acids, the side chains of these epimeric pairs are designated D or L. For example, when the group R is represented by the radical (a), $R^3$, $R^4$ and $R^5$ are hydrogen, and $R^6$ is methyl, said group can be:

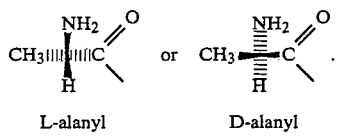

L-alanyl      D-alanyl

When the group R is represented by a radical which lacks an alpha-hydrogen, the alternative stereochemical designations R and S are preferred, e.g.,

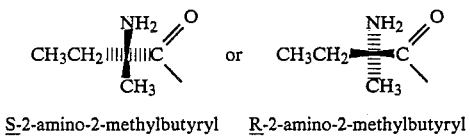

S-2-amino-2-methylbutyryl    R-2-amino-2-methylbutyryl

When a single diastereoisomer is desired as final product, it is preferred to employ an optically pure aminoacid as starting material, thus avoiding the processing of material which will have to be separated from the desired product (e.g., by column chromatography) at a later stage of the over-all processing.

Pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid. Pharmaceutically acceptable cationic salts include, but are not limited to, those of sodium, potassium, calcium, N,N'-dibenzylethylenediamine, N-methylglucamine (meglumine) and diethanolamine.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are hydrolyzed in vivo to the parent acid, having beta-lactamase activity. The preferred ester forming radicals are:

(5-methyl-1,3-dioxol-2-on-4-yl)methyl,
1H-isobenzofuran-3-on-1-yl,
gamma-butyrolacton-4-yl,
—$CHR^9OCOR^{10}$, and
—$CHR^9OCOOR^{10}$,
wherein $R^9$ is hydrogen or methyl and $R^{10}$ is ($C_1$–$C_6$)alkyl. More preferred radicals include pivaloyloxymethyl and 1-ethoxycarbonyloxyethyl.

When n is 1 and $R^1$ is 1,1-dioxopenicillanoyloxymethyl,

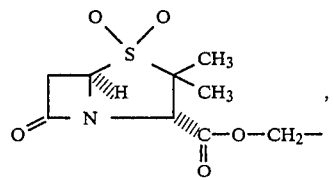

the compounds of the formulae (I) and (II) are diesters of methanediol. Such esters are also hydrolyzable under physiological conditions, yielding the parent acid of the formula (I) or (II), wherein n is 1 and $R^1$ is H, and penicillanic acid 1,1-dioxide. The latter compound also possesses beta-lactamase inhibitory activity. When n is 2 and $R^1$ is —$CH_2$—, the bis-ester is likewise hydrolyzed under physiological conditions, now producing two molecules of the parent acid from each molecule of the bis-ester.

Both the 6-beta-compounds (I) and the 6-alpha-compounds (II), regardless of C-6 stereochemistry are potent beta-lactamase inhibitors. When $R^1$ is a radical group forming an ester hydrolyzed in vivo, the preferred radicals are defined above.

The preferred values of R are glycyl [radical (a); $R^3$, $R^4$, $R^5$ and $R^6$=H], D- or L-alanyl [radical (a); $R^3$, $R^4$ and $R^5$=H; $R^6$=$CH_3$], L-valyl [radical (a); $R^3$; $R^3$, $R^4$ and $R^5$=H; $R^6$=($CH_3$)$_2$CH], L-seryl [radical (a); $R^3$, $R^4$ and $R^5$=H; $R^6$=$HOCH_2$], L-threonyl [radical (a); $R^3$, $R^4$ and $R^5$=H; $R^6$=$CH_3CH(OH)$], L-lysyl [radical (a); $R^3$, $R^4$ and $R^5$=H, $R^6$=$H_2N(CH_2)_4$], L-glutaminyl [radical (a); $R^3$, $R^4$ and $R^5$=H, $R^6$=$H_2NCO(CH_2)_2$], L-prolyl [radical (b); m=1; $R^3$ and $R^7$=H], trans-4-hydroxy-L-prolyl [radical (b); m=1; $R^3$=H; $R^7$=OH] and 2-amino-2-methylbutyryl [radical (a); $R^3$ and $R^4$=H; $R^5$ and $R^6$=$CH_3$].

The compounds of the formulae (I) and (II) are useful as inhibitors of beta-lactamase enzymes. By this mechanism, these compounds enhance the activity of beta-lactam antibiotics (penicillins and cephalosporins), particularly against those microorganisms which are resistant or partially resistant to the beta-lactam antibiotic through the production of enzymes (beta-lactamases) which would otherwise destroy or partially destroy the beta-lactam antibiotic. In this manner, the antibacterial spectrum of activity of the beta-lactam antibiotic is expanded.

The beta-lactam antibiotics are one of the most well-known and widely-used class of antibacterial agents. These compounds are characterized by a nucleus consisting of a 2-azetidinone (beta-lactam) ring. When the nucleus contains an attached thiazolidine ring, the compounds are usually referred to generically as penicillins, whereas when the nucleus contains an attached dihydrothiazine ring, the compounds are referred to as cephalosporins. While the present compounds are effective in enhancing the activity of beta-lactam antibiotics in general, their preferred use is found in their combination with a penicillin or cephalosporin of established clinical utility, viz., amoxicillin, ampicillin, apalacillin, azlocillin, azthreonam, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefonicid, cefmenoxime, cefodizime, cefoperazone, cefperazone, cefotaxime, cefotiam, cefotetan, cefoxitin, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, furazlucillin, hetacillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin and ticarcillin, including the pharmaceutically-acceptable salts thereof. The names employed for these beta-lactams are generally USAN, i.e., United States Adopted Names. Preferred combinations are with ampicillin or an ampicillin derivative, with amoxicillin or an amoxicillin derivative or with cefoperazone.

Although the compounds of the present invention can be administered separately from the beta-lactam antibiotic, combination dosage forms are preferred. The pharmaceutical composition, whether for oral or parenteral use, comprises in a ratio of 1:3 to 3:1 by weight a beta-lactamase inhibitor of the formula (I) or (II) and a beta-lactam antibiotic, in total amounts sufficient to successfully treat a bacterial infection in a mammal in a single or, more usually, multiple doses.

Also encompassed by the present invention are antibacterial compounds having the stereochemical formula

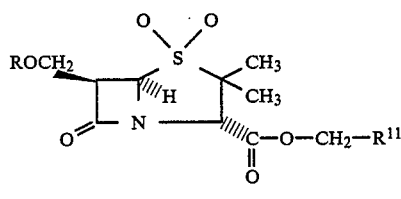

(III)

or

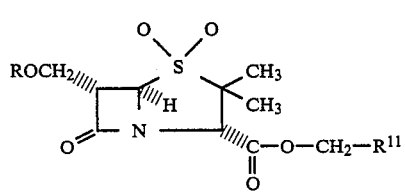

(IV)

wherein
R is as defined above; and
$R^{11}$ is an acyloxy radical derived from a conventional beta-lactam antibiotic such as one of those listed above. Preferred beta-lactam antibiotics for this purpose are derived from ampicillin or amoxicillin, represented by the acyloxy radical:

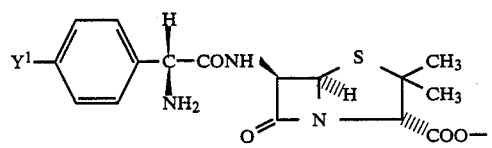

(e)

wherein $Y^1$ is
hydrogen,
hydroxy,
$(C_2-C_7)$-alkanoyloxy,
$(C_2-C_7)$-alkoxycarbonyloxy,
benzoyloxy, or
benzoyloxy monosubstituted with $(C_1-C_4)$-alkyl, $(C_1-C_4)$alkoxy or halo;

and the pharmaceutically-acceptable mono- and diacid addition salts thereof, the acids being as described above.

These bis-methanediol esters (III) and (IV) are effective as antibacterials through their in vivo hydrolysis to the corresponding beta-lactamase inhibitors of the formulae (I) and (II) wherein $R^1$ is hydrogen and to the corresponding beta-lactam antibiotic, such as preferred ampicillin, amoxicillin or amoxicillin substituted on phenolic oxygen. It will be further noted that such phenolic esters are also generally hydrolyzed in vivo to produce amoxicillin. The bis-methanediol ester compounds are formulated into pharmaceutical compositions, suitable for either parenteral or oral administration in single or (more usually) multiple dosage for the treatment of bacterial infections in mammals.

More preferred compounds of the formulae (III) and (IV) have $R^{11}$ in the form of the radical (e) with $Y^1$ as hydrogen or hydroxy; most preferred compounds have $Y^1$ as hydrogen.

Further encompassed by the present invention are intermediates of the stereochemical formula

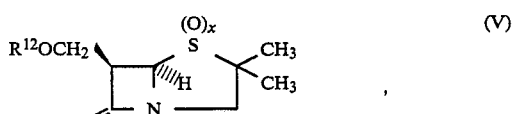

(V)

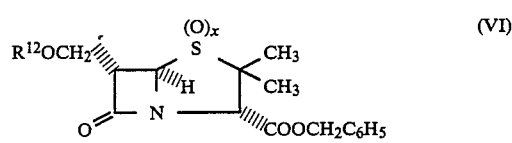

(VI)

wherein x is 0, 1 or 2; $R^{12}$ is

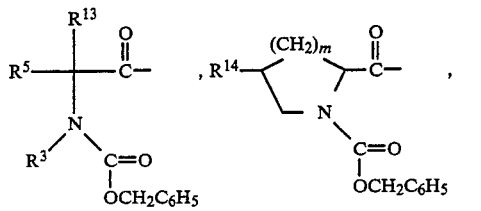

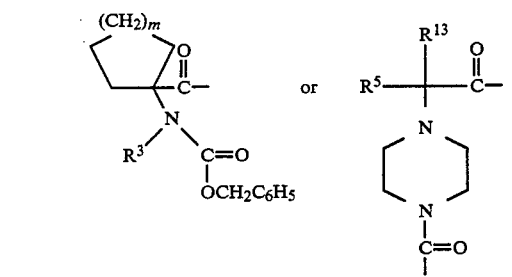

$R^3$ and $R^5$ are each independently hydrogen or $(C_1-C_3)$alkyl;
$R^{13}$ is hydrogen, $(C_1-C_6)$alkyl, phenyl or benzyl; or $(C_1-C_6)$ alkyl, phenyl or benzyl monosubstituted with

—COCH$_2$C$_6$H$_5$,

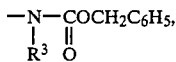

$-NR^8R^{15}$, $-NHCOR^3$, $-CONH_2$ or $-COOR^8$;
$R^8$ and $R^{15}$ are each independently $(C_1-C_{13})$alkyl;
$R^{14}$ is hydrogen, hydroxy,

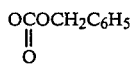

or $-OCOR^3$; and
m is 0, 1 or 2.

DETAILED DESCRIPTION OF THE INVENTION

Those compounds of the present invention of the formula (I) or (II) wherein n is 1 and $R^1$ is hydrogen are generally prepared by a sequence of steps from benzyl 6-beta-(hydroxymethyl)penicillanate and an alpha-amino acid. When the starting alpha-aminoacid contains no primary or secondary amino groups, no guanidino groups, and no substituent carboxy groups (such as the 4-carboxy group of glutamic acid), it can be used directly. However, such primary or secondary amino groups, or guanidino groups when present should be in protected form, preferably as a benzyloxycarbonyl (carbobenzoxy) derivative, and any substituent carboxy should be protected, preferably as a benzyl ester. When the direct coupling method (A), described below, is used it is preferable to also have free hydroxy groups protected as their benzyloxycarbonyl esters. Protected alpha-aminoacids employed in the present invention are encompassed by the formula $R^{12}$—OH, wherein $R^{12}$ is as defined above.

The required alpha-aminoacids are widely available commercially or according to methods disclosed in the literature, frequently already in protected form. When it is necessary to protect primary or secondary amino, hydroxy or guanidino groups with benzyloxycarbonyl groups, said protection is readily accomplished according to methods well known in the art, e.g., by treatment of the unprotected aminoacid with substantially one molar equivalent of benzyloxycarbonyl chloride (also called carbobenzoxy chloride or benzyl chloroformate) per amino or guanidino group in the alpha-amino acid, in a reaction inert solvent. When a hydroxy is also to be protected, an additional molar equivalent of benzyl chloroformate is employed together with one molar equivalent of a tertiary amine (e.g., triethylamine or pyridine).

alpha-Aminoacids containing substituent carboxy groups protected as benzyl ester are preferably prepared by standard methods from suitable precursors of the alpha-aminoacid moiety, e.g., 4-benzyloxy-carbonyl-2-aminobutyric acid is prepared from $HOOCCH_2CH_2CHO$, first forming the benzyl ester, then applying the Strecker synthesis to convert the aldehyde group to the desired aminoacid.

Various combinations of the following unit processes are employed for the stepwise conversion of the above starting materials to the desired products (I) and (II) wherein n is 1 and $R^1$ is hydrogen.

(A) Direct coupling of the alpha-aminoacid or protect-aminoacid (as delineated above) with the hydroxy group of a benzyl 6-hydroxymethylpenicillanate, its 1-oxide or its 1,1-dioxide; or (B) Said coupling accomplished via a trifluoromethanesulfonyl ester of said benzyl 6-hydroxymethylpenicillanate or its 1,1-dioxide;

(C) Oxidation of beta-lactam sulfur to sulfoxide (1-oxide) or sulfone (1,1-dioxide); or of 1-oxide to 1,1-dioxide;

(D) Removal of any benzyl ester and amino, hydroxy or amidino protecting groups by hydrogenolysis; and (E) When 6-alpha stereochemistry is desired, rearrangement of the 6-beta-substituent to 6-alpha.

Unit process (E) is carried out at a stage after unit process (C); and unit process (D) is obviously carried out after coupling (A) or (B), and is preferably carried out as the last stage. When the side chain of the product (I) or (II) contains thioether sulfur, oxidation (C) is carried out prior to coupling (A) or (B). When the side chain contains a sulfone group, any required oxidation of the side chain is conveniently done after the coupling, i.e., simultaneously with the oxidation of the beta-lactam sulfur. Generally preferred sequences for the 6-beta compounds (I) are: (B)(C)(D), (C)(B)(D) or (C)(A)(D). The generally preferred sequence for the 6-alpha compounds (II) is (C)(E)(A)(D).

In a variation of these processing steps, a 6-alpha-bromo-6-beta-(hydroxymethyl)penicillanate or 6-beta-bromo-6-alpha-(hydroxymethyl)penicillanate derivative is coupled with the aminoacid derivative according to unit processes (A) or (B). Reduction of the intermediate product with tributyltin hydride then provides, in either case, the 6-beta-(aminoacyl substituted hydroxymethyl)penicillanate derivative for any required further unit processing (C), (D) or (E). Notably, subsequent application of unit process (E) makes this method also useful for preparation of compounds in the 6-alpha series.

Unit Process (A)—Direct Coupling

The direct coupling of protected aminoacids (or amino acids not requiring protection) with a 6-(hydroxymethyl)penicillanate, its 1-oxide, or its 1,1-dioxide, is conveniently carried out by so-called dehydrative coupling, which is accomplished by using one of a wide variety of agents commonly used in peptide syntheses. Representative agents include N,N'-carbonyldiimidazole, N,N'-carbonyldi-s-triazine, and carbodiimides such as diisopropyl carbodiimide, dicyclohexylcarbodiimide, 1-cyclohexyl-3-(2-morpholinomethyl)carbodiimide, and 1-ethyl-3-(3'-dimethylaminopropyl)carbodiimide hydrochloride. In the present instance, the preferred reagent is diisopropylcarbodiimide, used in the presence of substantially one equivalent of a tertiary amine, preferably pyridine.

The temperature of the present coupling is not critical, temperatures in the range of 0°–50° C. being generally satisfactory. Temperatures low in the range, e.g., 0°–30° C., are generally preferred because of the sensitivity of the present beta-lactams to thermal degradation. Ambient temperatures (e.g., 20°–30°), which avoid the cost of heating or cooling, are generally satisfactory.

The coupling is accomplished in a reaction inert solvent. Here and hereinafter, "reaction-inert solvent" is defined as a solvent which does not react with starting materials, reagents, intermediates or products in a manner which significantly reduces the yield of the desired product. The variety of coupling agents which can be used to bring about the dehydrative coupling allow a wide choice of solvent. Representative solvents are N,N-dimethylformamide, tetrahydrofuran, dioxane, methylene chloride, nitromethane and acetonitrile. A preferred solvent with presently preferred diisopropylcarbodiimide is methylene chloride, since by-product urea is readily removed by simple filtration, and the solvent itself is readily removed by low temperature stripping in vacuo.

In the presently preferred coupling system, the molar ratio of the acid:hydroxymethylpenicillanate:coupling agent:tertiary amine is generally about 1:1:1:1 to 1.1:1:1.1:1.1. If desired, the products of the coupling reaction are generally purifiable by chromatography on silica gel, using chloroform or chloroform: ethyl acetate mixtures as eluant.

The preferred amino or hydroxy protecting group in the present instance is the benzyloxycarbonyl group (also called a carbobenzoxy group). Equivalent protecting groups will be obvious to those skilled in the art. The preferred penicillanate ester in the present instance is the benzyl ester. Again, equivalent groups will be obvious to those skilled in the art. Thus the present invention should not be so narrowly construed as to be limited to said benzyloxycarbonyl and benzyl groups.

Unit Process (B)—Coupling Via Active Ester

An alternative method of coupling protected amino acid (or of aminoacids not requiring protection) with the present benzyl hydroxymethyl penicillanates is to first convert the latter to an alkylating agent which will react directly with the amino acid derivative to form the desired ester bond. A presently preferred alkylating derivative is the trifluoromethanesulfonate ester, conveniently formed by reaction of 1 to 1.1 molar equivalents of trifluorosulfonic anhydride with the hydroxymethylpenicillanate in the presence of 1 to 2 molar equivalents of a tertiary amine (conveniently pyridine) in a reaction-inert solvent (conveniently $CH_2Cl_2$) at $-25°$ to $30°$ C. (preferably about $0°-5°$ C.).

The trifluoromethanesulfonate ester is then reacted with 1 to 1.2 molar equivalents of the above described protected amino acids in the presence of a tertiary amine (preferably triethylamine) at $0°-50°$ C., preferably ambient temperature (although, if desired, the reagents are mixed at lower temperature, e.g., $0°-5°$ C., to preclude possible exothermic warming).

Coupled products made by this route are generally of sufficient purity for direct use in the next process step, but, if desired, can be further purified by chromatography as described in the preceding section.

Unit Process (C)—Oxidation (S→$SO_2$)

Oxidation of the thio ether group of the penicillanate nucleus to the corresponding sulfone (1,1-dioxide) is readily accomplished with a permanganate salt such as $KMnO_4$, or with at least 2 molar equivalents of a per acid, conveniently, m-chloroperbenzoic acid, in a reaction inert solvent such as ethyl acetate, at $0°-50°$ C., conveniently at ambient temperature. When the oxidation is carried out after a thioether containing amino acid side chain is in place, the side chain sulfur will also be oxidized under these conditions, in which case 4 molar equivalents of the peracid are used in order to cleanly obtain the disulfone product. Unit Process C is preferably carried out prior to removal of N-benzyloxycarbonyl protecting groups.

If the sulfoxide (1-oxide) is desired as intermediate in this process, the thio ether group is simply oxidized by the same process, but only one molar equivalent of the oxidizing agent. When the intermediate is already in hand as the 1-oxide, it is further oxidized to the dioxide by the same process, using at least one molar equivalent of the oxidizing agent.

Unit Process (D)—Hydrogenolysis

Ultimate hydrogenolysis of any N-carbobenzoxy and benzyl ester groups is carried out by methods well-known in the penicillin art. The substrate, in a reaction-inert solvent, is contacted with hydrogen in the presence of a hydrogenation catalyst, usually Raney nickel or a noble metal catalyst, such as palladium, platinum or rhodium, optionally in the form of its oxide or a salt, or on a carrier such as carbon, an alkaline earth carbonate or alumina. The preferred catalyst is palladium, supported on carbon. Temperature is not critical (e.g. $0°-50°$ C. is suitable). Conveniently ambient temperature is employed. Thermal degradation is minimized, and yet the costs of heating or cooling are avoided. Pressure can be varied over a wide range (subatmospheric to 100 atmospheres), but as a matter of convenience will generally be in the range of 1 to 7 atmospheres. The reaction inert solvent is preferably relatively low boiling so as to be readily removed by concentration in vacuo. Aqueous tetrahydrofuran is a solvent particularly well-suited for the present purpose, since tetrahydrofuran can be stripped from the mixture to leave an aqueous residue from which purified product can be readily isolated by suitable extraction of impurities, isoelectric pH crystallization of the zwitterionic product, or lyophilization.

Unit Process (E)—Rearrangement

Rearrangement of 6-beta-substituted benzyl penicillanate 1,1-dioxides to 6-alpha-substituted benzyl penicillanate 1,1-dioxides is readily accomplished by contacting the former with substantially 1 molar equivalent of 1,5-diazabicyclo[4.3.0]non-5-ene (DBN) in a reaction-inert solvent such as methylene chloride at $0°-50°$ C., conveniently at ambient temperature, at which temperature a very short reaction time (usually only a few minutes) is required. Amino groups are preferably protected, conveniently with present benzyloxycarbonyl groups, as are hydroxy groups, conveniently protected in the present instance with trimethylsilyl groups. Such hydroxy groups are trimethylsilylated with substantially 1 equivalent of trimethylsilyl chloride in the presence of substantially 1 equivalent of a tertiary amine, conveniently pyridine, in a reaction-inert solvent such as $CH_2Cl_2$ at $0°-50°$ C., conveniently at ambient temperature. The trimethylsilyl group is readily removed by the action of protic solvents (acetic acid, water) used in quenching, isolation and purification.

Unit Process (F)—Formation of In vivo Hydrolyzable and Conjugate Esters

In vivo hydrolyzable esters [i.e., compounds of the formula (I) or (II), wherein n is 1 and $R^1$ is a radical group forming an ester which is hydrolyzable under physiological conditions] are preferably prepared from preformed compounds of the formula (I) or (II) wherein n is 1 and $R^1$ is hydrogen. When the side chain group R contains no primary or secondary amino, or carboxy group, [e.g.,

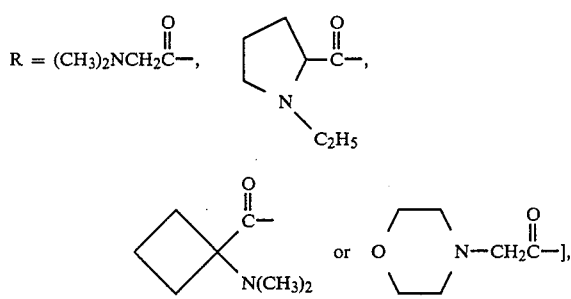

the acids (generally in cationic salt form, preferably the tetrabutylammonium salt) can be converted directly to the desired ester by known methods. The salts specified are generally reacted with a compound $R^{16}X$ wherein X is a typical nucleophilically displaceable group (such as mesylate or halide) and $R^{16}$ corresponds to $R^1$ when $R^1$ is an in vivo hydrolyzable ester radical, under typical nucleophilic displacement conditions. When the salt is a quaternary salt such as the tetrabutylammonium salt, the nucleophilic displacement reaction with such $R^{16}X$ compounds as (5-methyl-1,3-dioxol-2-on-4-yl)methyl bromide, 1H-isobenzofuran-3-on-1-yl bromide, chloromethyl pivalate, bromomethyl acetate or 1-ethoxycarbonyloxyethyl chloride occurs rapidly under mild conditions, e.g., at 0°–50° C., conveniently at ambient temperature, in a reactioninert solvent such as acetone. If a salt is not preformed from the acid, then the nucleophilic displacement will generally be carried out in the presence of one equivalent of a base, preferably a tertiary amine such as N,N-diisopropylethylamine.

When the side chain group R of the acids used for preparation of an in vivo hydrolyzable ester contains primary or secondary amino group(s), said group(s) are protected prior to ester formation. When $R^1$ represents an ester such as above —$CHR^9OCOR^{10}$ and —CHR$^9$OCOOR$^{10}$, the preferred amino protecting group is benzyloxycarbonyl, which is introduced using methods well-known in the art. For example, benzyl chloroformate is added slowly to the amine in a reaction-inert solvent such as aqueous acetone or aqueous tetrahydrofuran while maintaining pH 8.0 at a temperature of 0°–35° C., preferably 0°–20° C. In this manner, compounds are formed corresponding to the formulas (I) and (II) wherein n is 1 and $R^1$ is H, but side chain primary and secondary amino and amidino groups are substituted with a benzyloxycarbonyl group. The ester group is then introduced according to the methods provided in the preceding paragraph and protecting groups removed by hydrogenolysis according to Unit Process (D) above.

When $R^1$ represents an ester susceptible to hydrogenolysis, such as above (5-methyl-1,3-dioxol-2-on-4-yl)methyl or 1H-isobenzofuren-3-on-1-yl, the preferred protecting group for side chain primary or secondary amino groups(s) is:

(f)

wherein $R^8$ is ($C_1$-$C_3$)alkyl, as previously defined. Such derivatives, which are called enamines, are formed by reacting precursor acids, in the form of a cationic salt (preferably the tetrabutyl ammonium salt), with at least one equivalent of a ($C_1$-$C_3$)-alkyl acetoacetate (conveniently methyl acetoacetate) for each amine group present in the substrate, in a reaction-inert solvent at 10°–70° C. It is preferred to use an excess of the acetoacetate ester, in order to facilitate complete reaction, and indeed the ester itself can well serve as solvent for the reaction. In this manner, intermediate enamine compounds are produced. These correspond to the formula (I) or (II) wherein n is 1 and $R^1$ is hydrogen (in the form of a cationic salt), but any primary or secondary amino or guanidino groups are protected as enamine. Water formed in this process is generally removed either by use of a drying agent or by azeotropic distillation, e.g., with benzene.

The above enamine, still as the salt (preferably the tetrabutylammonium salt) is then reacted under the typical nucleophilic displacement conditions described above to form the desired in vivo hydrolyzable ester.

Finally the enamine protecting group(s) are removed by hydrolysis under mildly acidic conditions in an aqueous solvent, comprising simply water or water and a water miscible or immiscible reaction inert organic solvent; at 0°–50° C., conveniently at ambient temperature. The two phase system of water and ethyl acetate at ambient temperature represents particularly suitable conditions. Preferably, only one equivalent of a strong acid such as HCl or a sulfonate salt is used, and the product is isolated in the form of that acid addition salt.

The bis-methanediol esters (III) and (IV), as well as those of the formulae (I) and (II) wherein n is 1 and $R^1$ is 1,1-dioxopenicillanoyloxymethyl or wherein n is 2 and $R^1$ is —$CH_2$—, are also prepared from the same aminoacyl or protected benzyloxycarbonyl protected aminoacyl derivatives as are used for the preparation of the above in vivo hydrolyzable esters. In one alternative, the latter compounds are first converted to the corresponding chloromethyl esters. The preferred method is to convert the acid to its tetrabutylammonium salt, which is then reacted with excess chloromethyl bromide or iodide at 0°–50° C., preferably at 25° or less.

Although a chloromethyl ester can be used directly in the next step, it is preferred to first convert the chloromethyl ester to the corresponding iodomethyl ester. Contact of the chloromethyl ester with sodium iodide in acetone at 0°–50° until reaction is substantially complete represents conditions particularly well-suited to this purpose.

The iodomethylester is then reacted, in a reaction inert solvent at 0°–50° C., with a salt of penicillanic acid 1,1-dioxide; a salt of the same amino protected penicillanic acid used to make the chloromethyl ester; or the salt of a beta-lactam antibiotic which has side chain amino groups protected with benzyloxycarbonyl groups (alternatively, precursor azide is used to produce amino groups), and carboxy groups protected as benzyl ester. Exemplary of such betalactam antibiotic precursors are the penicillins listed above for use in combination with the present beta-lactamase inhibitors. Particularly valuable precursors are penicillin G, penicillin V, the side chain benzyl ester of carbenicillin, azidocillin, or an ampicillin or amoxicillin derivative of the formula

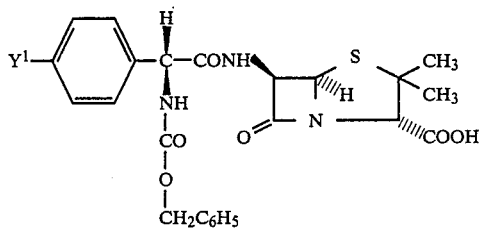

wherein $Y^1$ is H, benzyloxycarbonyloxy, $(C_2-C_7)$alkanoyloxy, $(C_2-C_7)$alkoxycarbonyloxy, benzoyloxy, or benzoyloxy mono-substituted with $(C_1-C_4)$alkyl, $(C_1-C_4)$alkoxy or halo (F, Cl or Br). The preferred salt is the tetrabutylammonium salt, since it reacts very rapidly with the iodomethyl ester, minimizing degradation.

In a second alternative, the bis-methanediol esters (III) and (IV), as well as the esters of the formula (I) or (II) where n is 1 and $R^1$ is 1,1-dioxopenicillanoyloxymethyl are prepared by reacting the salts of the same aminoacyl derivatives as are described above (for use in the preparation of the in vivo hydrolyzable esters) with a halomethyl ester (preferably an iodomethyl ester) of penicillanic acid 1,1-dioxide, or of a beta-lactam antibiotic having amino or carboxy groups protected according to the preceding paragraph.

In either alternative, any resulting azido containing or carbobenzoxy protected methanediol diester is converted to the desired end product of the formula (I), (II) [where n is 1 and $R^1$ is 1,1-dioxopenicillanoyloxymethyl or n is 2 and $R^1$ is —$CH_2$—], (III) or (IV) by hydrogenolysis, using methods detailed above; minimizing exposure to hydrolytic conditions which can cleave the sensitive methanediol ester bonds.

The above-defined pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. The pharmaceutically-acceptable mono- or diacid addition salts of the methanediol diesters containing two basic functions are prepared using one or two equivalents of the acid, as appropriate, according to the same methods.

The salts are alternatively isolated directly from a reaction mixture, i.e., without isolation of the free amine, otherwise using similar techniques of concentration and/or addition of a non-solvent.

The above-defined pharmaceutically-acceptable cationic salts of those compounds of the present invention having a free carboxylic acid group are also readily prepared by standard methods. For example, an equivalent of the corresponding cationic hydroxide, carbonate or bicarbonate or of an amine is combined with the carboxylic acid in an organic or aqueous solvent, preferably at reduced temperature (e.g., 0°–5° C.), with vigorous agitation and slow addition of the base. The salt is isolated by concentration and/or the addition of a non-solvent. If desired, the salt is isolated directly from a reaction mixture, without isolation of the free acid form, using the same techniques.

As indicated above, some of the compounds of the formula (I) and (II), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, Acta. Pathologica et Microbiologia Scandinav, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/tube). Twelve 2 fold dilutions of the test compound are employed, with initial concentration of the test drug being 200 mcg/ml. Tubes are read after 18 hours at 37° C. The susceptibility (MIC) of the test organism is accepted as the lowest concentration of compound capable of producing complete inhibition of growth as judged by the naked eye.

Those compounds of the formulae (I) and (II) having said in vitro antibacterial activity are thus useful as industrial antimicrobials, for example in water treatment, slime control, paint preservation and wood preservation, as well as for topical application as a disinfectant. In the case of use of these compounds for topical application, it is often convenient to admix the active ingredient with a nontoxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As also indicated above, the compounds of the formulae (I) and (II) are of more particular value as potent inhibitors of microbial beta-lactamases. By this mechanism they increase the antibacterial effectiveness of beta-lactam antibiotics (penicillins and cephalosporins) against many microorganisms, particularly those which produce a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) or (II) (having $R^1$ as hydrogen) alone, are determined. These MIC's are then compared with the MIC values obtained with a combination of the given antibiotic and the compound of the formula (I) or (II), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) enhance the antibacterial effectiveness of beta-lactam antibiotics in vivo. That is, they lower the amount of the antibiotic which is needed to protect mice against an otherwise lethal inoculum of certain beta-lactamase producing bacteria. In determining such activity, acute experimental infections are produced in mice, usually by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill 100 percent of the infected, non-treated control mice). The test compound in combination with the antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection). Compounds of the formulae (III) and (IV) are tested for in vivo activity in like manner, except that they are generally dosed alone, not in combination with other beta-lactam antibiotics.

In determining whether a particular strain of bacteria is sensitive to a particular compound of the formula (III) or (IV) it is not necessary to carry out an in vivo test. Instead, the MIC of a 1:1 molar mixture of a compound of the formula (I) or (II), wherein $R^1$ is hydrogen, and the component beta-lactam antibiotic, as appropriate, is measured according to the method above.

The ability of the compounds of formulae (I) and (II) to enhance the effectiveness of a beta-lactam antibiotic against beta-lactamase producing bacteria makes them valuable for coadministration with beta-lactam antibiotics in the treatment of bacterial infections in mammals, particularly man. In the treatment of a bacterial infection, the compound of the formula (I) or (II) can be comingled with the beta-lactam antibiotic, and the two agents thereby administered simultaneously. Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) to enhance the effectiveness of a beta-lactam antibiotic, it is preferred to administer a mixture of (I) or (II) with the beta-lactam antibiotic is administered preferably in single formulation, employing standard pharmaceutical carriers or diluents. A pharmaceutical composition comprising a pharmaceutically acceptable carrier, a beta-lactam antibiotic and a compound of formula (I) or (II) will normally contain from about 5 to about 80 percent of the pharmaceutically acceptable carrier by weight.

When using the compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula (I) or (II) and the beta-lactam antibiotic will normally be in the range from about 1:3 to 3:1 by weight. Additionally, when using the compounds of formula (I) or (II) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e. comingled) with a beta-lactam antibiotic which is effective only on parenteral administration, a combination formulation suitable for parenteral use will be required. When a compound of formula (I) or (II) is to be used simultaneously (comingled) with a beta-lactam antibiotic which is effective orally or parenterally, combinations suitable for either oral or parenteral administration can be prepared. Additionally, it is possible to administer preparations of the compounds of formula (I) orally, while at the same time administering a further beta-lactam antibiotic parenterally; and it is also possible to administer preparations of the compounds of formula (I) parenterally, while at the same time administering the further beta-lactam antibiotic orally. It is the capacity of compounds of the formula (III) or (IV) to hydrolyze in vivo and provide both a component beta-lactam antibiotic and a compound of the formula (I) or (II), wherein $R^1$ is hydrogen, which enhances the systemic activity and broadens the antibacterial spectrum of said compounds (III) and (IV) relative to the use of an equivalent amount of the beta-lactam antibiotic alone. When using the present antibacterial compounds of the formula (III) or (IV) for control of bacterial infections in a mammal, particularly man, the compound is administered alone, or mixed with pharmaceutically acceptable carriers or diluents. Said carrier or diluent is chosen on the basis of the intended mode of administration. For preferred, oral administration, tablets, capsules, lozenges, troches, powders, syrups, elixirs, aqueous solutions and suspensions, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

When using compounds of the formula (III) or (IV) to control bacterial infections, the daily dosage will be similar to that of other clinically used beta-lactam antibiotics. Although the prescribing physician will ultimately decide the dosage to be used in a human subject, the compounds of formula (III) or (IV) will normally be used orally at dosages in the range from about 10 to about 200 mg per kilogram of body weight per day, and parenterally at dosages from about 10 to about 100 mg per kilogram of body weight per day, usually in divided doses. In some instances, the prescribing physician will determine that dosages outside these limits are needed.

The present invention is illustrated by the following examples. However, it should be understood that the invention is not limited to the specific details of these examples. Unless otherwise specified, all operations were carried out at ambient temperature; all specified temperatures are in °C.; all solvent stripping was carried out in vacuo; all solvent drying was over $Na_2SO_4$; all pnmr (proton nuclear reasonance spectra) show delta values in ppm; those of Methods A, B, C and E are in $CDCl_3$ against a TMS (tetramethylsilane) reference; while those of method D are in $D_2O$ against a DSS (sodium 2,2-dimethyl-2-silapentane-5-sulfonate) reference.

The abbreviation TEA refers to triethylamine; THF refers to tetrahydrofuran; and atm refers to atmospheres (of hydrogen pressure).

METHOD A—DIRECT COUPLING OF PROTECTED AMINO ACIDS WITH BENZYL 6-(HYDROXYMETHYL)PENICILLANATES AND 1,1-DIOXIDES THEREOF

EXAMPLE A1

Benzyl 6-beta-(N-Benzyloxycarbonyl-L-prolyloxymethyl)-penicillanate 1,1-Dioxide

Benzyl 6-beta-(hydroxymethyl)penicillanate 1,1-dioxide (Kellogg, U.S. Pat. No. 4,287,181; 1.136 g, 0.0032 mole) and N-benzyloxycarbonyl-L-proline (0.881 g, 0.0035 mole) were dissolved in 10 ml $CH_2Cl_2$. Diisoproyl carbodiimide (0.551 ml, 0.0035 mole) and pyridine (0.258 ml, 0.0032 mole) were then added and the reaction mixture stirred 4.5 hours and filtered to remove urea. The $CHCl_2$ was stripped and replaced with ethyl acetate and the resulting solution washed in sequence with $H_2O$, dilute HCl, 5% $NaHCO_3$ and saturated NaCl, dried and stripped to light yellow oil, 2.252 g. The oil was chromatographed on silica gel with 9:1 $CHCl_3$:ethyl acetate as eluant and tlc monitoring ($R_f$ 0.5 using same eluant) to yield purified title product, 608 mg, pnmr 1.23 (3H, br. s), 1.50 (3H, s), 2.3–1.7 (4H, multiplet), 3.3–4.9 (8H, complex overlapping multiplets), 4.9–5.4 (4H, overlapping multiplets), 7.26 (5H, s), 7.31 (5H, s).

EXAMPLE A2

Benzyl 6-alpha-(N-benzyloxycarbonyl-glycyloxymethyl)-penicillanate 1,1-Dioxide

By the procedure of the preceding Example, using a reaction time of 20 minutes, benzyl 6-alpha-(hydroxymethyl)penicillanate 1,1-dioxide (Preparation E2; 0.656 g, 0.0018 mole) and N-benzyloxycarbonylglycine (0.388 g, 0.0018 mole) were converted to present purified title product, 0.744 g; tlc (9:1 $CHCl_3$:ethyl acetate) $R_f$ 0.4, (1:1 $CHCl_3$:ethyl acetate) $R_f$ 0.75; pnmr 1.22 (3H, s), 1.48 (3H, s), 3.91 (3H, m), 4.37 (1H, s), 4.49 (3H, m), 5.09 (2H, s), 5.13 (2H, AB q), 5.44 (1H, br. t), 7.31 (10H, s).

EXAMPLE A3

Benzyl 6-alpha-(N-Benzyloxycarbonyl-L-alanyloxymethyl)-penicillanate 1,1-Dioxide By the procedure of Example A1, using a 30 minute reaction time, benzyl 6-alpha-(hydroxymethyl)penicillanate 1,1-dioxide (0.364 g, 0.00103 mole) and N-benzyloxycarbonyl-L-alanine (0.230 g, 0.00103 mole) were converted to present purified title product, estimated to be 0.3 to 0.35 g, entire batch used in the next step (Example D12); tlc (9:1 $CHCl_3$:ethyl acetate) $R_f$ 0.4; pnmr 1.23 (3H, s), 1.38 (3H, d, J=7 Hz), 3.95 (1H, m, J=2, 5, 10 Hz), 4.2–4.7 (5H, overlapping multiplets), 5.11 (2H, s), 5.19 (2H, AB q), 5.47 (1H, br. d), 7.34 (10H, s).

EXAMPLE A4

Benzyl 6-alpha-(N-Benzyloxycarbonyl-L-prolyloxymethyl)-penicillanate 1,1-Dioxide By the procedure of Example A2, benzyl 6-alpha(hydroxymethyl)penicillanate 1,1-dioxide (0.325 g, 0.92 mmole) and N-benzyloxycarbonyl-L-proline (0.229 g, 0.92 mmole) were converted to present purified title product, 0.122 g; tlc (9:1 $CHCl_3$:ethyl acetate) $R_f$ 0.4; pnmr 1.26 (3H, br. s), 1.52 (3H, s), 1.7–2.3 (4H, overlapping multiplets), 3.2–4.1 (3 H, overlapping multiplets), 4.38 (1H, s), 4.1–4.6 (4H, overlapping multiplets), 4.7–5.4 (4H, overlapping multiplets), 7.35 (10H, s).

EXAMPLE A5

Benzyl 6-alpha-(N-Benzyloxycarbonyl-D-alanyloxymethyl)-penicillanate 1,1-Dioxide By the method of Example A1, using a reaction time of 2 hours, 6-alpha-(hydroxymethyl)penicillanate 1,1-dioxide (676 mg, 0.0019 mole) and N-benzyloxycarbonyl-D-alanine (0.427 g, 0.0019 mole) were converted to present purified title product, 0.888 g; pnmr 1.30 (3H, s), 1.36 (3H, d, J=7 Hz), 1.56, (3H, s), 3.8–4.7 (5H, overlapping multiplets), 4.38 (1H, s), 5.05 (2H, s), 5.14 (2H, AB q), 5.32 (1H, br. d), 7.28 (10H, s).

EXAMPLE A6

Benzyl 6-alpha-(N-Benzyloxycarbonyl-L-glutaminyloxymethyl)penicillanate 1,1-Dioxide By the method of Example A1, using a reaction time of 5 hours, 6-alpha-(hydroxymethyl)penicillanate 1,1-dioxide (0.534 g, 0.0015 mole) and N-benzyloxycarbonyl-L-glutamine (0.423 g, 0.0015 mole) were converted to present purified title product, 0.560 g; pnmr 1.24 (3H, s), 1.52 (3H, s), 1.8–2.4 (4H, m), 3.92 (1H, m), 4.1–4.55 (2H, m), 4.38 (1H, s), 4.64 (1H, d, J=2 Hz), 5.08 (2H, s), 5.17 (2H, AB q), 5.5–6.0 (3H, m), 7.3 (10H, s).

EXAMPLE A7

Benzyl 6-beta-(N-Benzyloxycarbonyl-N-methyl-glycyloxymethyl)penicillanate 1,1-Dioxide By the procedure of Example A1, benzyl 6-beta(hydroxymethyl)penicillanate 1,1-dioxide (2.15 g, 0.0061 mole) and N-benzyloxycarbonyl-N-methylglycine (1.5 g, 0.0067 mole) were converted to chromatographed title product; 0.70 g; tlc (9:1 $CHCl_3$:ethyl acetate) $R_f$ 0.5; pnmr 1.25 (3H, s), 1.52 (3H, s), 2.99 (3H, s), 4.44 (1H, s), 4.57 (1H, d, J=4Hz), 3.9–4.9 (5H, overlapping multiplets), 5.10 (2H, s), 5.21 (2H, ABq), 7.3–7.4 (10H, arom.).

EXAMPLE A8

Benzyl 6-beta-(N,N-Dimethylglycyloxymethyl)penicillanate 1,1-Dioxide

By the method of the preceding Examples, N,N-dimethylglycine is coupled with benzyl 6-beta(hydroxymethyl)penicillanate 1,1-dioxide to produce the instant title product.

EXAMPLE A9
Benzyl 6-alpha-(N,N-Diethylglycyloxymethyl)penicillanate 1,1-Dioxide By the method of the preceding Examples, N,N-diethylglycine is coupled with benzyl 6-alpha(hydroxymethyl)penicillanate 1,1-dioxide to produce the instant title product.

METHOD B—COUPLING OF PROTECTED AMINO ACIDS VIA 6-(TRIFLUOROSULFONYLOXYMETHYL)-PENICILLANATES

EXAMPLE B1
Benzyl 6-beta-(Trifluoromethylsulfonyloxymethyl)penicillanate

Benzyl 6-beta-(hydroxymethyl)penicillanate (Kellogg, U.S. Pat. No. 4,287,181; 1.755 g, 0.0055 mole) was dissolved in 25 ml $CH_2Cl_2$ and cooled to 0–5°. Pyridine (0.88 ml, 0.0108 mole) was added dropwise followed by trifluorosulfonic anhydride (1.02 ml, 0.0060 mole). After stirring for 20 minutes at 0–5°, the reaction mixture was diluted with $CH_2Cl_2$, washed in sequence with dilute HCl, $H_2O$ and saturated NaCl, dried and stripped to yield title product as a yellow oil, 2.2 g; pnmr 1.44 (3H, s), 1.62 (3H, s), 4.10 (1H, m, J=4, 5, 9 Hz), 4.45 (1H, s), 4.82 (2H, m, J=5, 9, 11 Hz), 5.19 (2H, s), 5.51 (1H, d, J=4 Hz), 7.37 (5H, s).

EXAMPLE B2
Benzyl 6-beta-(N-Benzyloxycarbonyl-D-alanyloxymethyl)-penicillanate Title product of the preceding Example (2.91 g, 0.0064 mole) was dissolved in 10 ml $CH_2Cl_2$. N-Benzyloxycarbonyl-D-alanine (1.72 g, 0.0077 mole) and TEA (0.979 ml, 0.0070 mole) were added, and the reaction mixture stirred 18 hours, diluted with $CH_2Cl_2$, washed with saturated NaCl, dried and stripped to a red oil. The oil was chromatographed on silica gel using $CHCl_3$ as eluant. Clean product fractions were combined and stripped to yield purified title product, 0.930 g; pnmr 1.37 (3H, d, J=7.5 Hz), 1.40 (3H, s), 1.59 (3H, s), 3.84 (1H, m), 4.32 (1H, m), 4.43 (1H, s), 4.47 (2H, m), 5.11 (2H, s), 5.17 (2H, s), 5.39 (1H, d, J=4 Hz), 5.17 (1H, br. d), 7.31 (5H, s), 7.36 (5H, s).

EXAMPLE B3
Benzyl 6-beta-(N-Benzyloxycarbonyl-L-alanyloxymethyl)-penicillanate Title product of Example B1 (14.31 g, 0.0315 mole) was dissolved in 80 ml $CH_2Cl_2$ and cooled to 0–5°. N-Benzyloxycarbonyl-L-alanine (8.46 g, 0.0379 mole) was added and the mixture stirred 3 minutes at 0–5°. TEA (4.83 ml, 0.0347 mole) was added dropwise over 4 minutes. After stirring 10 minutes at 0–5°, the bath was removed. After stirring 3 hours at ambient temperature, the reaction mixture was isolated according to the preceding Example. The light red oil (18.63 g) was chromatographed on silica gel, with 1:19 ethyl acetate:$CHCl_3$ as eluant, monitoring by tlc ($R_f$0.5 using the same eluant) to yield purified title product, 3.0 g; pnmr 1.38 (3H, d, J=7 Hz), 1.39 (3H, s), 1.59 (3H, s), 3.6–4.6 (3H, m), 4.40 (1H, s), 4.51 (1H, d, J=4 Hz), 5.07 (2H, s), 5.16 (2H, s), 5.38 (1H, d, J=4 Hz), 7.29 (5H, s), 7.33 (5H, s).

EXAMPLE B4
Benzyl 6-beta-(2-Benzyloxycarbonylamino-2-methylpropionyloxymethyl)penicillanate By the method of Example B2, title product of Example B1 (1.588 g, 0.0035 mole) and N-benzyloxycarbonyl-alpha-methylalanine (1.08 g, 0.0046 mole) were converted to crude title product as a red oil, 2.550 g, purified by chromatography according to the preceding Example, 224 mg; tlc (1:9 ethyl acetate: $CHCl_3$) $R_f$0.7; pnmr 1.39 (3H, s), 1.50 (6H, s), 1.60 (3H, s), 3.80 (1H, m), 4.38 (1H, s), 4.40 (2H, m), 5.04 (2H, s), 5.14 (2H, s), 5.27 (1H, br. s), 5.33 (1H, d, J=4 Hz), 7.28 (5H, s), 7.32 (5H, s).

EXAMPLE B5
Benzyl 6-beta-(N-Benzyloxycarbonyl-L-seryloxymethyl)-penicillanate By the method of Example B2, title product of Example B1 (1.89 g, 0.00417 mole) and N-benzyloxycarbonyl-L-serine (1.19 g, 0.00497 mole) were converted to crude title product as a light yellow oil, 1.00 g, which was chromatographed on silica gel with 1:1 ethyl acetate as eluant, monitoring by tlc ($R_f$0.55 using the same eluant) to yield a purified title product; 455 mg; pnmr 1.38 (3H,s), 1.59 (3H, s), 3.05 (1H, br. s), 3.6–4.1 (3H, m), 4.3–4.6 (4H, m), 5.08 (2H, s), 5.16 (2H, s), 5.35 (1H, d, J=4 Hz), 5.80 (1H, br. d, J=8 Hz), 7.28 (5H, s), 7.34 (5H, s).

EXAMPLE B6
Benzyl 6-beta-(N-Benzyloxycarbonyl-L-glutaminyloxymethyl)penicillanate By the method of Example B2, title product of Example B1 (2.80 g, 0.0061 mole) and N-benzyloxycarbonyl-L-glutamine (2.07 g, 0.0074 mole) were converted to crude title product, chromatographed according to the preceding Example to yield purified title product, 1.13 g; tlc (ethyl acetate), $R_f$0.5; pnmr 1.37 (3H, s), 1.56 (3H, s), 1.8–2.5 (4H, complex multiplet), 4.37 (1H, s), 3.5–4.6 (4H, complex multiplet), 5.04 (2H, s), 5.13 (2H, s), 5.34 (1H, d, J=4 Hz), 5.89 (3H, br. m), 7.27 (5H, s), 7.34 (5H, s).

EXAMPLE B7
Benzyl 6-beta-(N-Benzyloxycarbonyl-L-prolyloxymethyl)-penicillanate By the procedure of Example B2, title product of Example B1 (2.85 g, 0.0062 mole) and N-benzyloxycarbonyl-L-proline (1.87 g, 0.0075 mole), was converted to crude title product, purified by chromatography on silica gel with $CHCl_3$ as eluant, 1.00 g; tlc (9:1 $CHCl_3$:ethyl acetate) $R_f$0.7; pnmr 1.37 (3H, s), 1.65 (3H, s), 1.8–2.3 (4H, m), 3.3–4.0 (3H, m), 4.1–4.6 (4H, m), 5.0–5.15 (4H, m), [5.22 (0.33H, d, J=4 Hz), 5.36 (0.67H, d, J=4 Hz); revealing the 2:1 mixture of rotational isomers], 7.22–7.28 (10H, aromatic).

EXAMPLE B8

Benzyl 6-beta-(N-Benzyloxycarbonyl-trans-4-hydroxy-L-prolyloxymethyl)penicillanate By the procedure of Example B3, but using a reaction time of 4 hours and gradiently eluting on chromatography with 17:3, 4:1 and finally 7:3 CHCl$_3$:ethyl acetate, title product of Example B1 (9.3 g, 0.021 mole) and N-benzyloxycarbonyl-trans-4-hydroxy-L-proline (6.5 g, 0.025 mole) were converted to present title product as a white foam, 3.78 g; tlc (17:3 CHCl$_3$:ethyl acetate) R$_f$ 0.3; pnmr 1.36 (3H, s), 1.55 (3H, s), 2.0–2.3 (2H, m), 2.5 (1H, br. s), 3.3–3.9 (3H, m), 4.1–4.7 (5H, m), 5.10 (2H, m), 5.15 (2H, s), [5.24 (0.4H, d, J=4 Hz), 5.39 (0.6H, d, J=4 Hz), mixture of two rotational isomeric forms], 7.3–7.4 (10H, aromatic).

EXAMPLE B9

Benzyl 6-beta-[N,N'-Di(benzyloxycarbonyl)-L-lysyloxymethyl]penicillanate

By the procedure of Example B3, except to (1) use a reaction time of 18 hours after warming to room temperature, (2) strip away CH$_2$Cl$_2$ and replace it with ethyl acetate prior to the aqueous extractions and (3) use 9:1 CHCl$_3$:ethyl acetate on silica gel chromatography, title product of Example B1 (1.188 g, 0.00262 mole) and N,N'-di(benzyloxycarbonyl)-L-lysine (1.30 g, 0.00314 mole) were converted to purified title product as a light yellow oil, 0.760 g; tlc (9:1 CHCl$_3$:ethyl acetate) R$_f$ 0.25; pnmr 1.40 (3H, s), 1.58 (3H, s), 1.2–2.1 (6H, m), 3.12 (2H, m), 4.41 (1H, s), 3.6–4.6 (4H, m), 5.07 (4H, s), 5.15 (2H, s), 5.37 (1H, d, J=4 Hz), 5.51 (1H, br. d), 7.2–7.4 (15H, aromatics).

EXAMPLE B10

Benzyl 6-beta-(N-Benzyloxycarbonyl-L-methionyloxymethyl)penicillanate and

Benzyl 6-beta-(N-Benzyloxycarbonyl-D-methionyloxymethyl)penicillanate

By the procedure of the preceding Example, title product of Example B1 (1.332 g, 0.0029 mole) and N-benzyloxycarbonyl-dl-methionine (0.999 g, 0.0035 mole) were converted to a purified mixture of title products, 0.584 g; tlc (9:1 CHCl$_3$:ethyl acetate) R$_f$ 0.55; pnmr 1.40 (3H, s), 1.59 (3H, s), 2.08 (2H, m), 2.10 (3H, s), 2.53 (2H, m), 3.93 (1H, m), 4.1–4.7 (4H, m), 5.10 (2H, s), 5.16 (2H, s), 5.40 (1H, d, J=4 Hz), 5.43 (1H, br. d), 7.30 (10H, s).

EXAMPLE B11

Benzyl 6-beta-(N-Benzyloxycarbonyl-L-phenylalanyloxymethyl)penicillanate

By the method of Example B3, with purification by chromatography according to Example B7, title product of Example B1 (1.18 g, 0.0026 mole) and N-benzyloxycarbonyl-L-phenylalanine (0.935 g, 0.0031 mole) were converted to purified title product, 0.784 g; tlc (9:1 CHCl$_3$:ethyl acetate) R$_f$ 0.7; pnmr 1.41 (3H, s), 1.60 (3H, s), 3.06 (2H, d, J=6 Hz), 3.76 (1H, m), 4.41 (1H, s), 4.3–4.8 (3H, overlapping multiplets), 5.08 (2H, s), 5.17 (2H, s), 5.31 (1H, d, J=4 Hz), 7.23 (5H, s), 7.30 (5H, s), 7.35 (5H, s).

EXAMPLE B12

Benzyl 6-beta-(N-Benzyloxycarbonyl-L-valyloxymethyl)penicillanate

By the method of the preceding Example, title product of Example B1 (1.10 g, 0.00242 mole) and N-benzyloxycarbonyl-L-valine (0.732 g, 0.00288 mole) were converted to purified title product, 0.876 g; tlc (9:1 CHCl$_3$:ethyl acetate) R$_f$ 0.65; pnmr 0.87 (3H, d, J=7 Hz), 0.93 (3H, d, J=7 Hz), 1.40 (3H, s), 1.60 (3H, s), 2.10 (1H, m), 3.87 (1H, m), 4.40 (1H, s), 4.1–4.6 (3H, overlapping multiplets), 5.09 (2H, s, 5.17 (2H, s), 5.28 (1H, br. d), 5.39 (1H, d, J=4 Hz), 7.3 (10 H, aromatic).

EXAMPLE B13

Benzyl 6-beta-(N-Benzyloxycarbonyl-L-threonyloxymethyl)penicillanate

By the procedure of Example B11, title product of Example B1 (1.78 g, 0.00393 mole) and N-benzyloxycarbonyl-L-threonine (1.95 g, 0.0047 mole) were converted to purified title product, 0.100 g; tlc R$_f$ (ethyl acetate) 0.9; pnmr 1.22 (3H, d, J=6.5 Hz), 1.42 (3H, s), 1.63 (3H, s), 2.78 (1H, br. s), 3.7–4.6 (5H, overlapping multiplets), 4.42 (1H, s), 5.12 (2H, s), 5.18 (2H, s), 5.40 (1H, d, J=4 Hz), 5.58 (1H, br. d), 7.30 (5H, s), 7.33 (5H, s).

EXAMPLE B14

Benzyl 6-beta-(N-Benzyloxycarbonyl-L-seryloxymethyl)penicillanate and

Benzyl 6-beta-(N-Benzyloxycarbonyl-D-seryloxymethyl)penicillanate

By the procedure of Example B2, using 9:1 CHCl$_3$:ethyl acetate as eluant on chromatography, title product of Example B1 (1.0 g, 0.0022 mole) and N-benzyloxycarbonyl-dl-serine (0.633 g, 0.0026 mole) were converted to a mixture of present diastereomeric title products, 0.436 g.

EXAMPLE B15

Benzyl 6-beta-(N-Benzyloxycarbonylglycyloxymethyl)penicillanate

Title product of Example B1 (3.5 g, 0.0077 mole) was dissolved in 10 ml CH$_2$Cl$_2$ and cooled to 0–5°. N-Benzyloxycarbonyl glycine (1.93 g, 0.0092 mole) and then triethylamine (1.17 ml, 0.0085 mole) were added dropwise. The cooling bath was removed and the mixture stirred 18 hours and stripped of CH$_2$Cl$_2$ with replacement by ethyl acetate. The resulting solution was washed with H$_2$O and then saturated NaCl, dried and stripped to a yellow oil which was chromatographed on silica gel using 9:1 CHCl$_3$:ethyl acetate as eluant, monitoring by tlc (R$_f$ 0.6 using same eluant) to yield purified title product, 1.67 g, pnmr 1.39 (3H, s), 1.60 (3H, s), 3.7–4.0 (3H, overlapping multiplets), 4.42 (1H, s), 4.3–4.6 (2H, m), 5.09 (2H, s), 5.16 (2H, s), 5.39 (1H, d, J=4 Hz), 7.32 (5H, s), 7.35 (5H, s).

EXAMPLE B16

Benzyl 6-beta-Bromo-6-alpha-(trifluorosulfonyloxymethyl)-penicillanate 6-alpha-Bromo-6-beta-(hydroxymethyl)penicillanate (16.61 g, 41.5 mmoles) was dissolved in 100 ml $CH_2Cl_2$ and pyridine (6.72 ml, 0.083 mole) added. The resulting solution was added dropwise over 0.5 hour to a solution of trifluorosulfonic anhydride (9.78 ml, 0.058 mole) in 100 ml $CH_2Cl_2$ stirring at 0–5°. After stirring an additional 0.5 hour, the reaction mixture was stripped and the residue distributed between $H_2O$ and ethyl acetate. The organic layer was separated, washed in sequence with 2 portions $H_2O$, saturated $NaHCO_3$ and saturated NaCl, dried and stripped to yield title product, 19.92 g, pnmr 1.41 (s, 3H), 1.63 (s, 3H), 4.51 (s, 1H), 4.87 (s, 2H), 5.14 (s, 2H), 5.44 (s, 1H), 7.30 (s, 5H).

EXAMPLE B17

Benzyl 6-beta-Bromo-6-alpha-(N-benzyloxycarbonylglycyloxymethyl)penicillanate

Title product of the preceding Example containing C-6 epimer (1.56 g, 0.0029 mole) and N-benzyloxycarbonylglycine (0.736 g, 0.0035 mole) were reacted according to the procedure of Example B2. To isolate, the reaction mixture was stripped and the residue taken up into $H_2O$ and ethyl acetate. The pH was adjusted from 6 to 3 with dilute HCl and the organic layer separated, washed with saturated $NaHCO_3$ and then brine, dried, and stripped to yield title product as an oil, 1.57 g; ir 1776 $cm^{-1}$; pnmr shows a 1:3 mixture of 6-alpha-bromo:6-beta-bromo isomers based the ratio of C5-hydrogen peaks at 5.60 and 5.39 ppm.

EXAMPLE B18

Benzyl 6-beta-(N-Benzyloxycarbonylglycyloxymethyl)penicillanate

Title product of the preceding Example (1.57 g, 0.0027 mole; including the contained alpha-bromo isomer) was thoroughly dried by chasing with 3×10 ml benzene. The dried residue was taken up in 25 ml benzene, tributyltin hydride (2.1 ml, 0.009 mole) was added, and the mixture refluxed for 4 hours under $N_2$, then stripped and the residue triturated 3× with hexane and finally chromatographed on 100 g silica gel using 19:1 $CH_2Cl_2$:ethyl acetate as eluant monitoring by tlc ($R_f$ 0.4 using same eluant) to yield purified title product, 0.470 g; pnmr identical to the product of Example B15.

EXAMPLE B19

Benzyl 6-beta-(N-Benzyloxycarbonyl-L-leucyloxymethyl)-penicillanate

Title product of Example B1 (1.83 g, 0.0040 mole) and N-benzyloxycarbonyl-L-leucine (1.28 g, 0.0048 mole) were converted to present title product by the method of Example B9, except that $CHCl_3$ was used as the eluant on chromatography. The yield of purified title product was 0.94 g; light yellow oil; tlc (9:1 $CHCl_3$:ethyl acetate) $R_f$ 0.9.

EXAMPLE B20

Benzyl 6-alpha-(Trifluoromethylsulfonyloxymethyl)penicillanate 1,1-Dioxide

By the method of Example B1, benzyl 6-alpha(hydroxymethyl)penicillanate 1,1-dioxide is converted to present title product.

EXAMPLE B21

Benzyl 6-alpha-(N-Benzyloxycarbonyl-L-methionyloxymethyl)penicillanate 1,1-Dioxide By the method of Examples B2 to B15, title product of the preceding Example and N-benzyloxycarbonyl-L-methionine are reacted to form the instant title product.

EXAMPLE B22

Benzyl 6-alpha-(N-Isopropyl-L-prolyloxymethyl)-penicillanate 1,1-Dioxide

By the method of Examples B2 to B15, title product of Example B20 and N-isopropyl-L-proline are converted to present title product.

EXAMPLE B23

Benzyl 6-alpha-[N,N'-Di(benzyloxycarbonyl)-L-arginyloxymethyl]penicillanate 1,1-dioxide By the method of Examples B2 to B15, title product of Example B20 and N,N'-di(benzyloxycarbonyl)-L-arginine are converted to instant title product.

EXAMPLE B24

Benzyl 6-alpha-[L-(2-benzyloxycarbonylamino-4-methoxycarbonylbutyryl)oxymethyl]penicillanate 1,1-Dioxide By the method of Examples B2 to B15, title product of Example B20 and methyl N-benzyloxycarbonylgamma-glutamate are converted to instant title product.

EXAMPLE B25

Benzyl 6-alpha-(N-benzyloxycarbonyltyrosyloxymethyl)-penicillanate 1,1-Dioxide

By the method of Examples B2 to B15, title product of Example B20 and N-benzyloxycarbonyltyrosine are converted to present title product.

EXAMPLE B26

Benzyl 6-alpha-[L-(2-Benzyloxycarbonylamino-4-benzyloxycarbonylbutyryl)oxymethyl]penicillanate 1,1-Dioxide By the method of Examples B2 to B15, title product of Example B20 and benzyl N-benzyloxycarbonyl-gamma-glutamate are converted to present title product.

METHOD C—OXIDATION OF PENICILLANATES TO PENICILLANATE 1,1-DIOXIDES

EXAMPLE C1

Benzyl 6-beta-(N-Benzyloxycarbonyl-D-alanyloxymethyl)-penicillanate 1,1-Dioxide

Title product of Example B2 (0.93 g, 0.0017 mole) was dissolved in 5 ml ethyl acetate. m-Chloroperbenzoic acid (0.915 g, 0.0053 mole) was added and the mixture stirred 18 hours, diluted with ethyl acetate, washed in sequence with 5% NaHSO$_3$, 5% NaHCO$_3$ and saturated NaCl, dried and stripped to yield title product, 0.858 g; pnmr 1.25 (3H, s), 1.40 (3H, d, J=7 Hz), 1.52 (3H, s), 3.9–4.9 (5H, m), 4.45 (1H, s), 5.08 (2H, s), 5.18 (2H, AB q), 5.37 (1H, br. d), 7.29 (5H, s), 7.32 (5H, s).

EXAMPLE C2

Benzyl 6-beta-(N-Benzyloxycarbonyl-L-alanyloxymethyl)-penicillanate 1,1-Dioxide

By the method of the preceding Example, title product of Example B3 (3.0 g, 0.0057 mole) was converted to present title product, white foam, 2.95 g; pnmr 1.26 (3H, s), 1.41 (3H, d, J=7.5 Hz), 1.52 (3H, s), 3.9–5.0 (5H, m), 4.46 (1H, s), 5.09 (2H, s), 5.21 (2H, AB q), 5.23 (1H, br. d), 7.33 (5H, s), 7.39 (5H, s).

EXAMPLE C3

Benzyl 6-beta-(2-Benzyloxycarbonylamino-2-methylpropionyloxymethyl)penicillanate 1,1-Dioxide By the method of Example C1, title product of Example B4 (0.224 g, 0.41 mmole) was converted to present title product as a colorless oil, 0.250 g; pnmr 1.24 (3H, s), 1.51 (9H, s), 3.98 (1H, m), 4.42 (1H, s), 4.2–5.0 (3H, m), 5.04 (2H, s), 5.20 (3H, m), 7.31 (5H, s), 7.37 (5H, s).

EXAMPLE C4

Benzyl 6-beta-(N-Benzyloxycarbonyl-L-seryloxymethyl)-penicillanate 1,1-Dioxide

By the procedure of Example C1, title product of Example B5 (0.455 g, 0.83 mmole) was converted to present title product, 0.495 g, pnmr 1.25 (3H, s), 1.52 (3H, s), 3.47 (1H, br. s), 4.47 (1H, s), 3.6–5.0 (7H, m), 5.13 (2H, s), 5.20 (2H, AB q), 5.94 (1H, br, d, J=8 Hz), 7.34 (5H, s), 7.39 (5H, s).

EXAMPLE C5

Benzyl 6-beta-(N-Benzyloxycarbonyl-L-glutaminyloxylmethyl)penicillanate 1,1-Dioxide By the procedure of Example C1, but using a 3 hour reaction time, title product of Example B6 (1.13 g, 0.0019 mole) was converted to present title product, 0.864 g; pnmr 1.24 (3H, s), 1.50 (3H, s), 1.8–2.4 (4H, complex), 4.44 (1H, s), 3.8–5.0 (5H, complex multiplet), 5.08 (2H, s), 5.20 (2H, AB q), 5.4–6.0 (3H, br. m), 7.29 (5H, s), 7.36 (5H, s).

EXAMPLE C6

Benzyl 6-beta-(N-Benzyloxycarbonyl-L-prolyloxymethyl)-penicillanate 1,1-Dioxide

By the method of Example C1, title product of Example B7 (1.0 g, 0.0018 mole) was converted to present title product, 1.0 g, pnmr identical with that prepared by Example A1.

EXAMPLE C7

Benzyl 6-beta-[N,N'-Di(benzyloxycarbonyl)lysyloxymethyl]penicillanate 1,1-Dioxide By the method of Example C1, title product of Example B9 (0.76 g, 0.0010 mole) was converted to present title product as a white foam, 765 mg; pnmr 1.22 (3H, s), 1.47 (3H, s), 1.1–2.0 (6H, m), 3.10 (2H, m), 4.44 (1H, s), 3.7–4.9 (5H, overlapping multiplets), 5.07 (4H, s), 5.17 (2H, AB q), 5.58 (1H, br. d), 7.2–7.4 (15H, aromatic).

EXAMPLE C8

Benzyl 6-beta-[L-(2-Benzyloxycarbonylamino-4-methanesulfonylbutyryl)oxymethyl]penicillanate 1,1-Dioxide and Benzyl 6-beta-[D-(2-Benzyloxycarbonylamino-4-methanesulfonylbutyryl)oxymethyl]penicillanate 1,1-Dioxide By the method of Example C1, but using 6 rather than 3 equivalents of m-chloroperbenzoic acid and a 4 hour reaction time, the mixed title products of Example B10 (0.584 g, 0.001 mole) were converted to a mixture of present diastereomeric title products as a light yellow oil, 0.556 g; pnmr 1.23 (3H, s), 1.50 (3H, s), 2.30 (2H, m), 2.85 (3H, s), 3.06 (2H, m), 3.8–4.9 (6H, overlapping multiplets), 5.04 (2H, s), 5.16 (2H, AB q), 5.71 (1H, br. d), 7.24 (5H, s), 7.28 (5H, s).

EXAMPLE C9

Benzyl 6-beta-(N-Benzyloxycarbonyl-L-phenylalanyloxymethyl)penicillanate 1,1-Dioxide By the method of Example C1, title product of Example B11 (0.784 g, 0.0013 mole) was converted to present title product as a light yellow oil, 0.755 g; pnmr 1.20 (3H, s), 1.51 (3H, s), 3.08 (2H, d), 4.01 (1H, m), 4.44 (1H, s), 4.3–4.8 (4H, overlapping multiplets), 5.07 (2H, s), 5.22 (2H, AB q), 5.34 (1H, br. d), 7.1–7.4 (15H, aromatic).

EXAMPLE C10

Benzyl 6-beta-(N-Benzyloxycarbonyl-L-valyloxymethyl)-penicillanate 1,1-Dioxide

By the method of Example C1, title product of Example B12 (0.876 g, 0.0015 mole) was converted to present title product as a colorless oil, 0.808 g; pnmr 0.87 (3H, d, J=7 Hz), 0.98 (3H, d, J=7 Hz), 1.24 (3H, s), 1.51 (3H, s), 2.16 (1H, m), 4.44 (1H, s), 3.7–4.9 (5H, overlapping multiplets), 5.08 (2H, s), 5.18 (2H, AB q), 7.30 (5H, s), 7.34 (5H, s).

EXAMPLE C11

Benzyl 6-beta-(N-Benzyloxycarbonyl-L-threonyloxymethyl)-penicillanate 1,1-Dioxide By the method of Example C1, title product of Example B13 (100 mg, 0.17 mmole) was converted to present title product as an oil, 109 mg; pnmr 1.21 (3H, d, J=7 Hz), 1.26 (3H, s), 1.50 (3H, s), 2.87 (2H, br. s), 4.43 (1H, s), 4.0–4.9 (6H, overlapping multiplets), 5.07 (2H, s), 5.17 (2H, AB q), 5.65 (1H, br. d), 7.3 (10H, aromatic).

EXAMPLE C12

Benzyl 6-beta-(N-Benzyloxycarbonyl-L-seryloxymethyl)-penicillanate 1,1-Dioxide and Benzyl 6-beta-(N-Benzyloxycarbonyl-D-seryloxymethyl)-penicillanate 1,1-Dioxide By the procedure of Example C1, mixed title products of Example B14 (0.436 g, 0.80 mmole) were converted to present mixed diastereomeric products as a colorless oil, 0.400 g.

EXAMPLE C13

Benzyl 6-beta-(N-Benzyloxycarbonylglycyloxymethyl)penicillanate 1,1-Dioxide

By the method of Example C1, title product of Examples B15 and B18 (1.67 g, 0.0032 mole) was converted to present title product, purified by chromatography on silica gel with 9:1 $CHCl_3$:ethyl acetate as eluant, monitoring by tlc (Rf 0.4 with same eluant), 1.42 g; pnmr 1.28 (3H, s), 1.53 (3H, s), 3.85–4.20 (3H, overlapping multiplets), 4.46 (1H, s), 4.3–4.7 (3H, overlapping multiplets), 5.12 (2H, s), 5.22 (2H, ABq), 5.42 (1H, br, t), 7.31 (5H, s), 7.38 (5H, s).

EXAMPLE C14

Benzyl 6-beta-(N-Benzyloxycarbonyl-L-leucyloxymethyl)-penicillanate 1,1-Dioxide

By the method of Example C1, title product of Example B19 (0.940 g, 0.0016 mole) was converted to present title product, 0.20 g; pnmr 0.92 (6H, d), 1.23 (3H, s), 1.52 (3H, s), 1.1–1.7 (3H, overlapping multiplets), 4.47 (1H, s), 3.9–5.0 (5H, overlapping multiplets), 5.09 (2H, s), 5.20 (2H, ABq), 5.44 (1H, d), 7.31 (5H, s), 7.35 (5H, s).

EXAMPLE C15

Benzyl 6-beta-(N-Benzyloxycarbonyl-trans-4-hydroxy-L-prolyloxymethyl)penicillanate 1,1-Dioxide By the procedure of Example C1, title product of Example B8 (3.5 g, 0.0062 mole) was converted to present title product, initially isolated as a white foam, 3.79 g, which was further purified by chromatography on 160 g silica gel with 1:1 $CHCl_3$:ethyl acetate as eluant and tlc monitoring (Rf 0.5 using same eluant) isolated as a second white foam, 2.3 g; pnmr 1.24 (3H, br, s), 1.49 (3H, s), 2.0–2.4 (2H, m), 3.5–3.7 (2H, m), 4.0–4.8 (7H, overlapping multiplets), 4.8–5.3 (4H, overlapping multiplets), 7.31 (5H, s), 7.36 (5H, s).

METHOD D—HYDROGENOLYSIS OF BENZYL AND BENZYLOXYCARBONYL GROUPS

EXAMPLE D1

6-beta-(D-Alanyloxymethyl)penicillanic Acid 1,1-Dioxide

10% Pd/C (0.5 g) was stirred in 5 ml $H_2O$ and hydrogenated under 4 atmospheres of $H_2$ for 20 minutes. Title product of Example C1 (0.858 g) in 5 ml THF was added and hydrogenation at 4 atmospheres continued for 30 minutes. The catalyst was recovered by filtration with $H_2O$ and THF wash. The THF was stripped from the combined filtrate and wash, and the pH of the aqueous residue adjusted from 3.0 to 5.0 with dilute NaOH, partially stripped and finally lyophilized to yield title product, 0.448 g; ir 1789 cm$^{-1}$; pnmr 1.46 (3H, s), 1.59 (3H, s), 1.62 (3H, d, J=7 Hz), 4.33 (1H, s), 4.0–4.9 (4H, m), 5.08 (1H, d, J=4 Hz).

EXAMPLE D2

6-beta-(L-Alanyloxymethyl)penicillanic Acid 1,1-Dioxide

10% Pd/C (2 g) in 15 ml $H_2O$ was pre-hydrogenated at 4 atmospheres $H_2$ for 20 minutes. Title product of Example C2 (2.95 g) in 10 ml THF was added and hydrogenation at 4 atmospheres continued 20 minutes. Catalyst was recovered by filtration with $H_2O$/THF wash. The combined filtrate and wash was stripped of THF (pH 2.3). Title product crystallized (as the zwitterion) on concentration of the aqueous residue, 0.860 g; mp 205°–207° ; ir 1808 cm$^{-1}$; pnmr (DCl added) 1.51 (3H, s), 1.61 (3H, d, J=7 Hz), 1.63 (3H, s), 4.1–4.9 (4H, m), 4.71 (1H, s), 5.18 (1H, d, J=4 Hz).

EXAMPLE D3

6-beta-(2-Amino-2-methylpropionyloxymethyl)penicillanic Acid 1,1-Dioxide

By the procedure of Example D1, title product of Example C3 (0.250 g) was converted to present title product, 100 mg; ir 1785 cm$^{-1}$; pnmr 1.46 (3H, s), 1.58 (3H, s), 1.66 (6H, s), 4.29 (1H, s), 4.2–5.0 (3H, m), 5.06 (1H, d, J=4 Hz).

EXAMPLE D4

6-beta-(L-Seryloxymethyl)penicillanic Acid 1,1-Dioxide

By the procedure of Example D1, title product of Example C4 (0.495 g) was converted to present title product, 230 mg; ir 1785 cm$^{-1}$; pnmr 1.47 (3H, s), 1.60 (3H, s), 3.9–5.0 (7H, complex multiplets), 5.05 (1H, d, J=4 Hz).

EXAMPLE D5

6-beta-(L-Glutaminyloxymethyl)penicillanic Acid 1,1-Dioxide

By the procedure of Example D1, title product of Example C5 (0.864 g) was converted to present title product, 0.595 g; ir 1786 cm$^{-1}$; pnmr 1.50 (3H, s), 1.61 (3H, s), 2.0–2.7 (4H, complex multiplet), 4.1–5.3 (5H, complex multiplet), 4.68 (1H, s).

EXAMPLE D6

6-beta-(L-prolyloxymethyl)penicillanic Acid 1,1-Dioxide

By the procedure of Example D1, without adjusting the aqueous pH, but washing with ethyl acetate before lypohilization, title product of Example A1 and C6 (0.608 g) was converted to present title product, 0.287 g; ir 1793 cm$^{-1}$; pnmr 1.48 (3H, s), 1.60 (3H, s), 2.17 (4H, m), 3.43 (2H, m), 4.54 (1 H, s), 4.1–5.0 (4H, m), 5.12 (1H, d, J=4 Hz).

EXAMPLE D7

6-beta-(L-lysyloxymethyl)penicillanic Acid 1,1-Dioxide

By the procedure of the preceding Example, using a 30 minute hydrogenation time, title product of Example C7 (0.765 g) was converted to present title product, 0.291 g; ir 1790 cm$^{-1}$; pnmr 1.47 (3H, s), 1.60 (3H, s), 1.5–2.3 (6H, m), 3.02 (2H, m), 4.30 (1H, s), 4.1–5.0 (4H, complex multiplets), 5.08 (1H, d, J=4 Hz).

EXAMPLE D8

6-beta-[L-(2-Amino-4-methanesulfonylbutyryl)oxymethyl]penicillanic Acid 1,1-Dioxide and 6-beta-[D-(2-Amino-4-methanesulfonylbutyryl)oxymethyl]penicillanic acid 1,1-Dioxide By the method of Example D6, mixed title products of Example C8 (0.556 g) were converted to present title mixture of diastereomeric products, 190 mg; ir 1796 cm$^{-1}$; pnmr 1.50 (3H, s), 1.62 (3H, s), 2.54 (2H, m), 3.17 (3H, s), 3.52 (2H, m), 4.0–5.0 (5H, overlapping multiplets), 5.14 (1H, d, J=4 Hz).

EXAMPLE D9

6-beta-(L-Phenylalanyloxymethyl)penicillanic Acid 1,1-Dioxide

By the procedure of Example D6, title product of Example C9 (0.755 g) was converted to present title product, 0.295 g; ir 1792 cm$^{-1}$; pnmr 1.48 (3H, s), 1.60 (3H, s), 3.33 (2H, m), 4.4–4.9 (5H, complex), 5.05 (1H, d, J=4 Hz), 7.40 (5H, aromatic).

EXAMPLE D10

6-beta-(L-Valyloxymethyl)penicillanic Acid 1,1-Dioxide

By the procedure of Example D6, title product of Example C10 (0.808 g) was converted to present title product, 0.370 g; ir 1799 cm$^{-1}$; pnmr 1.08 (3H, d, J=1 Hz), 1.10 (3H, d, J=7 Hz), 1.53 (3H, s), 1.64 (3H, s), 2.37 (1H, m), 4.12 (1H, d, J=4 Hz), 4.72 (1H, s), 4.2–5.0 (3H, overlapping multiplets), 5.20 (1H, d, J=4 Hz).

EXAMPLE D11

6-beta-(L-Threonyloxymethyl)penicillanic Acid 1,1-Dioxide

By the procedure of Example D6, title product of Example C11 (109 mg) was converted to present title product, 50 mg; ir 1808 cm$^{-1}$; pnmr 1.36 (3H, d, J=7 Hz), 1.49 (3H, s), 1.60 (3H, s), 4.13 (1H, d, J=4 Hz), 4.45 (1H, s), 4.2–5.0 (4H, overlapping multiplets), 5.12 (1H, d, J=4 Hz).

EXAMPLE D12

6-alpha-(L-Alanyloxymethyl)-penicillanic Acid 1,1-Dioxide

By the procedure of Example D6 the entire batch of title product of Example A3 was converted to instant title product, 300 mg, pnmr 1.49 (3H, s), 1.62 (3H, s), 1.64 (3H, d, J=7 Hz), 4.0–4.8 (4H, overlapping multiplets), 4.47 (1H, s), 5.08 (1H, d, J=2 Hz).

EXAMPLE D13

6-alpha-(L-Prolyloxymethyl)-penicillanic Acid 1,1-Dioxide

By the procedure of Example D6, title product of Example A4 (122 mg) was converted to instant title product, 55 mg, ir 1787 cm$^{-1}$; pnmr 1.47 (3H, s), 1.61 (3H, s), 1.9–2.5 (4H, overlapping multiplets), 3.47 (2H, m), 4.18 (1H, m), 4.33 (1H, s), 4.1–4.9 (3H, overlapping multiplets), 5.05 (1H, d, J=2 Hz).

EXAMPLE D14

6-alpha-(D-Alanyloxymethyl)-penicillanic Acid 1,1-Dioxide

By the procedure of Example D6, title product of Example A5 (0.888 g) was converted to instant title product; 0.433 g; ir 1786 cm$^{-1}$; pnmr 1.49 (3H, s), 1.62 (3H, s), 1.64 (3H, d, J=6 Hz), 4.0–4.3 (2H, overlapping multiplets), 4.38 (1H, s), 4.3–4.8 (2H, complex multiplet), 5.08 (1H, d, J=2 Hz).

EXAMPLE D15

6-alpha-(D-Glutaminyloxymethyl)-penicillanic Acid 1,1-Dioxide

By the procedure of Example D6, title product of Example A6 (0.560 g) was converted to instant title product, 0.255 g; ir 1794 cm$^{-1}$; pnmr 1.50 (3H, s), 1.64 (3H, s), 2.0–2.8 (4H, complex, multiplet), 4.1–4.4 (2H, m), 4.55 (1H, s), 4.5–4.9 (2H, m), 5.08 (1H, d, J=2 Hz).

EXAMPLE D16

6-alpha-(Glycydoxymethyl)-penicillanic Acid 1,1-Dioxide

By the procedure of Example D6, title product of Example A2 (0.744 g) was converted to present title product, 0.325 g, ir 1790 cm$^{-1}$; phmr 1.48 (3H, s), 1.61 (3H, s) 4.04 (2H, s), 4.19 (1H, m), 4.42 (1H, s), 4.75 (2H, m), 5.08 (1H, d, j)=2 Hz).

EXAMPLE D17

6-alpha-(L-Seryloxymethyl)-penicillanic Acid 1,1-Dioxide and 6-alpha-(D-Seryloxymethyl)-penicillanic Acid 1,1-Dioxide By the procedure of Example D1, using a hydrogenation time of 30 minutes, mixed title products of Example C12 (0.400 g) were converted to present diastereometic mixture of title products, 0.200 g; ir 1783 cm$^{-1}$.

EXAMPLE D18

6-beta-(Glycyloxymethyl)penicillanic Acid 1,1-Dioxide

Title product of Example A7 and C13 (0.143 g) was dissolved in 6 ml of 1:4:1 ethyl acetate:methanol:H$_2$O and added to 143 mg 10% Pd/C slurried in 6 ml of the same solvent mixture. The mixture was hydrogenated for 0.5 hour at 4 atmospheres, the catalyst was recovered by filtration, the organic solvents were stripped, ethyl acetate added to the aqueous residue, and the pH adjusted from 2.5 to 4.6 with dilute NaOH. The aqueous phase was separated and freeze dried to yield title product as a foam, 81 mg; ir 1773 cm$^{-1}$; pnmr 1.46 (3H, s), 1.59 (3H, s), 4.02 (2H, s), 4.33 (1H, s), 4.3–5.0 (3H, overlapping multiplets, 5.10 (1H, d, J=4Hz).

EXAMPLE D19

6-beta-(L-Leucyloxymethyl)penicillanic Acid 1,1-Dioxide

Title product of Example C14 (0.70 g) was dissolved in 10 ml THF and added to 0.50 g 10% Pd/C slurried in 10 ml H$_2$O. The mixture was hydrogenated at 4 atmospheres for 20 minutes, catalyst was recovered by filtration, THF was stripped, the pH was adjusted to 5.5 with dilute NaOH, and the H$_2$O lyophilized to yield instant title product, 0.20 g; ir 1785 cm$^{-1}$; pnmr 0.93 (6H, m), 1.42 (3H, s), 1.53 (3H, s), 1.3–1.9 (3H, overlapping multiplets), 3.9–5.1 (6H, overlapping multiplets).

EXAMPLE D20

6-beta-(trans-4-hydroxy-L-prolyloxymethyl)-penicillanic Acid 1,1-Dioxide

By the procedure of Example D1, title product of Example C15 (2.34 g) was hydrogenated, without pH adjustment during isolation, to yield instant title product as a white crystalline powder, 1.1 g; pnmr 1.48 (3H, s), 1.60 (3H, s), 2.2–2.6 (2H, m), 3.2–3.7 (2H, m), 4.43 (1H, s), 4.4–5.0 (5H, overlapping multiplets), 5.12 (1H, d, J=4Hz).

EXAMPLE D21

6-beta-(N-Methylglycyloxymethyl)penicillanic Acid 1,1-Dioxide

By the procedure of Example D1, title product of Example A7 (0.70 g) was hydrogenated, without pH adjustment during isolation, but extracting the aqueous residue with ethyl acetate prior to lyophilization, to yield instant title product as a crystalline white solid, 0.45 g; pnmr 1.50 (3H, s), 1.61 (3H, s), 2.84 (3H, s), 4.08 (2H, s), 4.48 (1H, s), 4.3–5.0 (3H, overlapping multiplets), 5.13 (1H, d, J=4Hz).

EXAMPLE D22

By the procedure of the preceding Examples, title products of Examples B21 to B25, A8 and A9 are converted, respectively, to:

6-alpha-(L-methionyloxymethyl)penicillanic acid 1,1-dioxide;
6-alpha-(N-isopropyl-L-prolyloxymethyl)penicillanic acid 1,1-dioxide;
6-alpha-(L-arginyloxymethyl)penicillanic acid 1,1-dioxide;
6-alpha-[L-(2-amino-4-methoxycarbonylbutyryl)oxymethyl]penicillanic acid 1,1-dioxide;
6-alpha-(L-tyrosyloxymethyl)penicillanic acid 1,1-dioxide;
6-alpha-(L-alpha-glutamyloxymethyl)penicillanic acid 1,1-dioxide;
6-beta-(N,N-dimethylglycycloxymethyl)penicillanic acid 1,1-dioxide; and
6-alpha-(N,N-diethylglycyloxymethyl)penicillanic acid 1,1-dioxide.

EXAMPLE D23

Pivaloyloxymethyl 6-alpha-(Glycyloxymethyl)-penicillanate 1,1-Dioxide

Title product of Example F2 (1.8 g) is hydrogenated in 60 ml 2:1 THF:H$_2$O over 1.8 g 10% Pd/C at 4 atmospheres for 1.5 hours. The catalyst is recovered by filtration, the filtrate stripped of THF and the aqueous residue lyophylized to yield instant title product.

By the same method, other products of Example F2 are converted to:
acetoxymethyl 6-alpha-(glycyloxymethyl)penicillanate 1,1-dioxide;
1-ethoxycarbonyloxyethyl 6-alpha-(glycyloxymethyl)-penicillanate 1,1-dioxide; and
pivaloyloxymethyl 6-beta-(trans-4-hydroxy-L-prolyl)-penicillanate 1,1-dioxide.

EXAMPLE D24

6-beta-(D-2-Amino-2-phenylacetamido)-penicillanoyloxymethyl 6'-alpha-(Glycyloxymethyl)penicillanate 1',1'-Dioxide Title compound of Example F5 (1.4 g) is combined with 30 ml of methylene chloride and 30 ml of isopropyl alcohol and hydrogenated at 4 atmospheres over 2.0 g of 10% Pd/C until substantially 2 equivalents of H$_2$ are taken up. An additional portion (1.5 g) of catalyst is added if hydrogenation stops prematurely and hydrogenation continued. The catalyst is recovered by filtration with 1:1 methylene chloride:isopropyl alcohol wash. The combined filtrate and wash are concentrated in vacuo to yield title product.

By the same method other products of Example F5 are converted, for example, to:
6-beta-(D-2-amino-2-phenylacetamido)penicillanoyloxymethyl 6'-beta(trans-4-hydroxy-L-prolyloxymethyl)penicillanate 1,1-dioxide (from the corresponding azidocillin derivative or from the derivative wherein Y" is hydrogen);
6-beta-[D-2-amino-2-(4-hydroxyphenyl)acetamido]-penicillanoyloxymethyl 6'-alpha-(glycyloxymethyl)-penicillanate 1',1'-dioxide (from the corresponding derivative wherein Y" is benzyloxycarbonyloxy;
various 6-beta-[D-2-amino-2-(4-acyloxyphenyl)acetamido]penicillanoyloxymethyl esters, depending on the value of Y";
0 6-beta-(phenylacetamido)penicillanoyloxymethyl 6'-alpha-(glycyloxymethyl)penicillanate 1',1'-dioxide;
6-beta-(phenoxyacetamido)penicillanoyloxymethyl 6'-beta-(trans-4-hydroxy-L-prolyloxymethyl)penicillanate 1',1'-dioxide; and
6-beta-(2-carboxy-2-phenylacetamido)penicillanoyloxymethyl 6'-alpha-(glycyloxymethyl)penicillanate 1',1'-dioxide.

EXAMPLE D25

6-beta-(Glycyloxymethyl)-1,1-dioxopenicillanoyloxymethyl 6-[D-2-Amino-2-phenylacetamido]penicillanate Pd/C (10%, 2 g) is prehydrogenated in 20 ml of water. A solution of title product of Example F8 (0.98 g, 1.226 mmoles) in 30 ml THF is added, and the mixture hydrogenated for 1.5 hours at 4 atmospheres. Catalyst is recovered by filtration over diatomaceous earth with THF and H$_2$O wash. THF is removed from the combined filtrate and washes by concentration in vacuo. The aqueous residue is extracted 3×30 ml ethyl acetate and freeze dried to yield title product.

EXAMPLE D26

By the method of the preceding Example, N-protected products of Example F9 and F12 are converted to:
1,1-dioxopenicillanoyloxymethyl 6-alpha-(glycyloxymethyl)penicillanate 1,1-dioxide; and
1,1-dioxopenicillanoyloxymethyl 6-beta-(trans-4-hydroxy-L-prolyloxymethyl)penicillanate 1,1-dioxide;
methylene bis-[6-alpha-(glycyloxymethyl)-1,1dioxopenicillanate]; and
methylene bis-[6-beta-(trans-4-hydroxy-L-prolyl)-1,1-dioxopenicillanate].

METHOD E—REARRANGEMENT OF 6-beta-(HYDROXYMETHYL)PENICILLANATE DERIVATIVES TO 7-alpha(HYDROXYMETHYL)PENICILLANATE DERIVATIVES

PREPARATION E1

Benzyl 6-beta-(Trimethylsilyloxy-methyl)penicillanate 1,1-Dioxide

Benzyl 6-beta-(hydroxymethyl)penicillanate 1,1-dioxide (Kellogg, U.S. Pat. No. 4,287,181; 0.509 g, 0.0014 mole) was dissolved in 5 ml $CH_2Cl_2$. Pyridine (0.226 ml, 0.0028 mole) and then trimethylsilyl chloride (0.201 ml, 0.00154 mole) were each added dropwise, and the reaction mixture stirred 18 hours. Like quantities of pyridine and trimethylsilyl chloride were then added and stirring continued for 5 hours, at which time the reaction mixture was diluted with ethyl acetate, washed with $H_2O$ and then saturated NaCl, dried, stripped and the residue triturated with 1:1 hexane:ether to yield title product as a white solid, 0.472 g, pnmr 0.15 (9H, s), 1.26 (3H, s), 1.53 (3H, s), 3.78–4.38 (3H, m), 4.46 (1H, s), 4.62 (1H, d, J=4 Hz), 5.22 (2H, AB q), 7.36 (5H, s).

PREPARATION E2

Benzyl 6-alpha-(hydroxymethyl)penicillanate 1,1-Dioxide

Title product of the preceding Preparation (0.472 g, 0.0011 mole) was dissolved in 5 ml $CH_2Cl_2$. DBN (1,5-diazabicyclo[4.3.0]non-5-ene (0.125 ml, 0.0011 mole) was added dropwise and the mixture stirred 3 minutes, then quenched with acetic acid (0.10 ml, 0.0022 mole), diluted with $CH_2Cl_2$, washed with water and stripped to crude product, 348 mg. The latter was chromatographed on silica gel with 9:1 $CHCl_3$:ethyl acetate as eluant and tlc monitoring ($R_f$ 0.2 with same eluant) to yield purified title product, 0.178 g; pnmr 1.28 (3H, s), 1.54 (3H, s), 3.05 (1H, br), 3.7–4.2 (3H, m), 4.41 (1H, s), 4.68 (1H, d, J=2 Hz), 5.19 (2H, AB q), 7.33 (5H, s).

METHOD F—FORMATION OF IN VIVO HYDROLYZABLE AND CONJUGATE ESTERS

EXAMPLE F1

6-alpha-(N-Benzyloxycarbonylglycyloxymethyl)-penicillanic Acid 1,1-Dioxide

Title product of Example D16 (3.0 g), is dissolved in 100 ml 1:1 $H_2O$:THF. The pH is adjusted and maintained at 8.3–8.7 as benzyl chloroformate (1.79 g) is added dropwise over several minutes. Following a brief period of stirring the pH is adjusted to 6.0 with 1N HCl and THF removed by distillation in vacuo. The aqueous residue is extracted with 30 ml of ethyl acetate and the extract discarded. Fresh ethyl acetate (50 ml) is added and the pH adjusted to 1.8 with 1N HCl. The aqueous layer is extracted with 50 ml fresh ethyl acetate. The combined organic layer and extract is washed 1×50 ml saturated NaCl, dried and evaporated in vacuo to yield title product.

The title product of Example D20 is converted to the corresponding N-benzyloxycarbonyl derivative by use of the same acylation procedure.

EXAMPLE F2

Pivaloyloxymethyl 6-alpha-(N-Benzyloxycarbonyl-glycyloxymethyl)penicillanate 1,1-Dioxide The title product of the preceding Example 6.75 g) and N,N-diisopropylethylamine (3.34 ml) are dissolved in dimethylformamide (50 ml), chloromethyl pivalate (2.72 ml) is added, and the mixture allowed to stir for 20 hours. The reaction mixture is diluted with ethyl ether (300 ml), washed with water (2×100 ml), dried and evaporated in vacuo to an oil. The oil is dissolved in 100 ml ether, washed 3×50 ml $H_2O$, dried and concentrated in vacuo to yield purified title product.

The same method, but substituting an equivalent amount of bromomethyl acetate or 1-ethoxycarbonyloxyethyl chloride, as appropriate, is used to prepare the corresponding acetoxymethyl and 1-ethoxycarbonyloxyethyl 6-alpha-(N-benzyloxycarbonyl-glycyloxymethyl)penicillanate 1,1-dioxides.

By the same method the 6-beta-(N-benzyloxycarbonyl-trans-4-hydroxy-L-prolyloxymethyl)penicillanic acid 1,1-dioxide of the preceding Example and 6-alpha-(N,N-dimethylglycyloxymethyl)penicillanic acid 1,1-dioxide of Example D22 are converted to the corresponding pivaloyloxymethyl esters.

EXAMPLE F3

Chloromethyl 6-alpha-(N-Benzyloxycarbonylglycyloxymethyl)-penicillanate 1,1-Dioxide Title product of Example F1 (1 g) is combined with 10 ml of methylene chloride and 2 ml of water and the pH adjusted to 8.0 with 40% tetrabutylammonium hydroxide over a period of 15 minutes. The methylene chloride layer is separated and the aqueous layer extracted with three 2 ml portions of fresh methylene chloride. The methylene chloride layers are combined, dried over $Na_2SO_4$, and concentrated in vacuo to yield the tetrabutylammonium salt. The salt is combined with 10 ml of chloroiodomethane, the mixture stirred for 16 hours, and concentrated to dryness in vacuo to yield present title product.

By the same method, the corresponding 6-beta hydroxyprolyl derivative of Example F2 is converted to its chloromethyl ester.

EXAMPLE F4

Iodomethyl 6-alpha-[N-(Benzyloxycarbonyl)glycyloxymethyl]-penicillanate 1,1-Dioxide Title product of the preceding Example (0.24 g) is combined with 3 ml of acetone and sodium iodide (0.58 g) and the mixture stirred for 16 hours. The reaction mixture is concentrated in vacuo and the residue distributed between 7.5 ml of ethyl acetate and 5.0 ml of water. The ethyl acetate is separated, washed in sequence with two 25 ml portions of water and one 25 ml portion of brine, dried over $Na_2SO_4$ and concentrated in vacuo to provide present title product.

By the same method, the other chloromethyl ester of the preceding Example is converted to its iodomethyl ester.

EXAMPLE F5

6-beta-(D-2-Azido-2-phenylacetamido)penicillanoyloxymethyl 6'-alpha-[N-(Benzyloxycarbonyl)glycyloxymethyl]-penicillanate 1',1'-Dioxide A mixture of 3.5 g of 6-beta-(D-2-azido-2-phenylacetamido)penicillanic acid (azidocillin) sodium salt in 20 ml of methylene chloride and 20 ml of water was treated with sufficient 6N hydrochloric acid to give a pH of 2.0. Tetrabutylammonium hydroxide (40% in water) was gradually added until the pH was 7.0. The organic phase was separated and the aqueous layer further extracted (2×20 ml) with fresh methylene chloride. The methylene chloride layers were combined, dried over sodium sulfate and concentrated under vacuum to give 4.2 g of the corresponding tetrabutylammonium salt.

The tetrabutylammonium salt (1.65 g, 2.7 mmoles) and the title iodomethyl ester of the preceding Example (2.7 mmoles) are combined in 20 ml of acetone and stirred to dissolve. After 15 minutes, the reaction mixture is concentrated in vacuo to yield title product.

By the same method, the other iodomethyl ester of the preceding Example is converted to the corresponding bis-methanediol ester with 6-beta-(D-2-azido-2-phenylacetamido)penicillanic acid.

By the same method, both iodomethyl esters of the preceding Example are reacted with the tetrabutylammonium salts of compounds of the formula

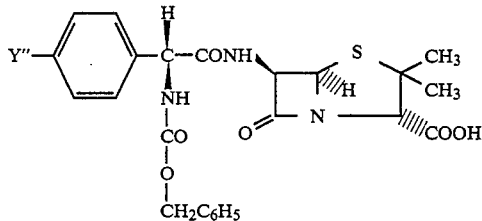

wherein Y″ is hydrogen, benzyloxycarbonyloxy, acetoxy, isopropionyloxy, adipoyloxy, isovaleroyloxy, ethoxycarbonyloxy, isobutyroyloxy, benzoyloxy, o-chlorobenzoyloxy, m-bromobenzoyloxy, m-fluorobenzoyloxy, m-ethylbenzoyloxy or p-methoxybenzoyloxy to yield the corresponding methanediol bis-esters.

By the same method, both iodomethyl esters of the preceding Example are reacted with the tetrabutylammonium salts of penicillin G, penicillin V and alphabenzyloxycarbonylbenzyl penicillin (i.e., the side chain benzyl ester of carbenicillin) to yield the corresponding methanediol bis-esters.

EXAMPLE F6

Chloromethyl 6-[D-(2-Azido-2-phenylacetamido)]penicillanate

A solution of 12.0 g (0.03 mole) 6-[D-(2-azido-2-phenylacetamido)penicillanic acid sodium salt, 25 ml water was combined with 100 ml methylene chloride and 10.17 g (0.03 mole) tetrabutylammonium hydrogen sulfate. The mixture (pH 3.0) was adjusted to pH 7.5 with sodium bicarbonate, the organic layer is separated and the aqueous layer was extracted with 2×100 ml methylene chloride. The combined organic layers were dried (Na$_2$SO$_4$) and the solvent evaporated to yield a solid residue. The residue was triturated with ethyl acetate (300 ml), filtered, the cake washed with ethyl acetate followed by ethyl ether and dried under nitrogen to afford 16.5 g (89%) of tetrabutylammonium salt.

A mixture of 12.32 g (0.02 mole) of the above salt was combined with 70 ml chloroiodomethane and the mixture stirred overnight at ambient temperature. The reaction mixture was concentrated to dryness and the residue purified by chromatography on 600 g silica gel, eluting with 1:1 ethyl acetate/hexane by volume to afford 8.1 g (95%) of the desired chloromethyl ester as a pale yellow viscous oil, pnmr/CDCl$_3$: 1.58 (s, 3H), 1.68 (s, 3H), 4.45 (s, 1H), 5.1 (s, 1H), 5.5–5.9 (dd m, 4H), 7.2 (d, 1H) and 7.4 (s, 5H) ppm.

Chloromethyl 6-[2-azido-2-(p-acetoxyphenyl)acetamido]penicillanate is obtained in like manner.

EXAMPLE F7

Iodomethyl 6-[D-(2-Azido-2-phenylacetamido)]penicillanate

Title product of the preceding Example (1.45 g, 0.00342 mole) in 30 ml acetone was purged 3 minutes with N$_2$. NaI (2.55 g, 0.01714 mole) was added and the resulting solution stirred 16 hours at ambient temperature. The reaction mixture was clarified by filtration, the filtrate concentrated in vacuo, and the residue taken into 75 ml CHCl$_3$ and filtered. The CHCl$_3$ filtrate was washed 2×30 ml saturated NaCl, dried (Na$_2$SO$_4$) and concentrated to yield title product as a foam, 1.23 g, pnmr/CDCl$_3$/TMS/delta (ppm): 1.53 (3H, s), 1.64 (3H, s), 4.37 (1H, s), 5.05 (1H, s), 5.56 (2H, m, J=4, 11 Hz), 5.87 (2H, ABq), 7.31 (5H, s).

Iodomethyl 6-[2-azido-2-(p-acetoxyphenyl)acetamido]penicillanate is obtained in like manner.

EXAMPLE F8

6-beta-(N-Benzyloxycarbonylglycyloxymethyl)-1,1-dioxopenicillanoyloxymethyl 6-[D-(2-Azido-2-phenylacetamido)]penicillanate Title product of Example D18 is converted to its N-benzyloxycarbonyl derivative according to Example F1. The resulting product (0.58 g, 1.43 mmoles) is dissolved in 50 ml CH$_2$Cl$_2$. H$_2$O (20 ml) is added and the pH adjusted to 8.6 with 1N NaOH. NaHCO$_3$ (0.121 g, 1.43 mmoles) is added followed by tetrabutylammonium hydrogen sulfate (0.488 g, 1.43 mmoles) in portions, while maintaining pH 8.0–8.3 with 1N NaOH, until near the end of the addition, when the pH is allowed to drop to 7.0. After stirring the mixture 15 minutes, the layers are separated. The aqueous layer is extracted 1×30 ml fresh CH$_2$Cl$_2$. The combined organic layer and extract are dried and concentrated in vacuo to yield tetrabutylammonium 6-beta-(N-benzyloxycarbonylglycyloxymethyl)penicillanate 1,1-dioxide. The latter is dissolved in 20 ml acetone and added to a solution of title product of the preceding Example (0.714 g, 1.43 mmoles) in 15 ml acetone and the mixture stirred 1 hour at ambient temperature, concentrated in vacuo and the residue slurried in 30 ml of ethyl acetate to yield crystalline tetrabutylammonium iodide recovered by filtration. The filtrate is evaporated to yield title product.

EXAMPLE F9

1,1-Dioxopenicillanoyloxymethyl 6-alpha-(N-Benzyloxycarbonylglycyloxy-methyl)-penicillanate 1,1-Dioxide Title product of Example F1 (0.51 g, 1.26 mmoles) is dissolved in 50 ml CH$_2$Cl$_2$ H$_2$O (10 ml) is added and the pH adjusted to 8.6 with 1N NaOH. NaHCO$_3$ (0.106 g, 1.26 mmoles) and then tetrabutylammonium hydrogen sulfate (0.428 g, 1.26 mmoles) is added. The pH is adjusted to 7.5 with 1N NaOH. After stirring 30 minutes at ambient temperature, the organic layer is separated, dried and concentrated in vacuo to yield tetrabutylammonium 6-alpha-(N-benzyloxycarbonylglycyloxymethyl)penicillanate 1,1-dioxide. The latter is dissolved in 20 ml of acetone. Iodomethyl penicillanate 1,1-dioxide (prepared, for example, according to Godtfredsen et al., U.S. Pat. No. 4,342,772; 0.47 g) in 15 ml acetone is added and the mixture stirred for 5 minutes, and then concentrated in vacuo. The residue is slurried in 30 ml of ethyl acetate and crystalline tetrabutylammonium iodide recovered by filtration. The filtrate is concentrated in vacuo. The residue is reslurried in 30 ml of ethyl acetate and any additional tetrabutylammonium iodide recovered by filtration. The last filtrate is concentrated in vacuo to yield title product.

By the same method, the other product of Example F1 and 6-alpha-(N-isopropyl-L-prolyloxymethyl)-penicillanic acid 1,1-dioxide of Example D22 are converted, respectively, to:
1,1-dioxopenicillanoyloxymethyl 6-beta-(N-benzyloxycarbonyl-trans-4-hydroxy-L-prolyloxymethyl)-penicillanate 1,1-dioxide; and
1,1-dioxopenicillanoyloxymethyl 6-alpha-(N-isopropyl-L-prolyloxymethyl)penicillanate 1,1-dioxide.

EXAMPLE F10

Chloromethyl 6-alpha-(N-Benzyloxycarbonylglycyloxymethyl)-penicillanate 1,1-Dioxide By the method of Example F8, title product of Example F1 (0.396 g, 1.0 mmole) is converted to its tetrabutylammonium salt. The latter is dissolved in 30 ml bromochloromethane, stirred at ambient temperature for 18 hours, and concentrated in vacuo to yield title product.

Chloromethyl 6-beta-(N-benzyloxycarbonyl-trans-4-hydroxy-L-prolyloxymethyl)penicillanate and chloromethyl 6-alpha-(N,N-diethylglycyloxymethyl)penicillanate are prepared in like manner from corresponding products of Examples D20 and D22, respectively.

EXAMPLE F11

Iodomethyl 6-alpha-(N-Benzyloxycarbonylglycyloxymethyl)-penicillanate 1,1-Dioxide Title product of the preceding Example (0.25 g, 0.55 mmole) is dissolved in 15 ml of acetone and purged with $N_2$. NaI (0.42 g, 2.8 mmoles) is added and the resulting solution stirred 17 hours and then concentrated in vacuo. The solids are triturated with $CHCl_3$, insolubles removed by filtration and title product recovered from filtrate by concentration in vacuo.

In like manner, the other chloromethyl esters of the preceding Example are converted to corresponding iodomethyl esters.

EXAMPLE F12

Methylene bis-[6-alpha-(N-Benzyloxycarbonylglycyloxymethyl)-1,1-dioxopenicillanate]

Title product of Example F1 (0.17 g, 0.42 mmole) is converted to its tetrabutylammonium salt according to the procedure of Example F10. The latter is dissolved in 10 ml acetone and added to a solution of title product of the preceding Example (0.23 g, 0.42 mmole) in 10 ml acetone. The mixture is stirred 15 minutes, concentrated to a foam in vacuo and the foam slurried in 20 ml ethyl acetate. The slurry is filtered to yield tetrabutylammonium iodide and the filtrate concentrated in vacuo to yield title product.

By the same method, the other iodomethyl esters of the preceding Example are reacted with their corresponding salts to obtain methylene bis-[6-beta-(N-benzyloxycarbonyl-trans-4-hydroxy-L-prolyloxymethyl)-1,1-dioxopenicillanate] and methylene bis-[6-alpha-(N,N-diethylglycyloxymethyl)-1,1-dioxopenicillanate].

EXAMPLE F13

Tetrabutylammonium 6-alpha-(Glycyloxymethyl)penicillanate 1,1-Dioxide

To a solution of 6-alpha-(glycyloxymethyl)penicillanic acid 1,1-dioxide (0.53 g, 2.0 mmoles) in 50 ml $CHCl_3$ was added tetrabutylammonium hydroxide (1.3 ml of 1.53N, 2.0 mmoles). After stirring 5 minutes, the organic layer was separated, dried and evaporated to yield title product.

EXAMPLE F14

Tetrabutylammonium 6-alpha-[N-(2-methoxycarbonyl-1-methylvinyl)-glycyloxymethyl]penicillanate 1,1-Dioxide Title product of the preceding Example (0.81 g) is dissolved in 1 ml methyl acetoacetate and heated at 60° for 15 minutes under $N_2$. The mixture is cooled, diluted with 75 ml benzene and concentrated in vacuo to yield title product, all of which is used directly in the next step.

EXAMPLE F15

(5-Methyl-1,3-dioxol-2-on-4-yl)methyl 6-alpha-[N-(2-Methoxycarbonyl-1-methylvinyl)-glycyloxymethyl]penicillanate 1,1-Dioxide The entire batch of title product from the preceding Example in 20 mL of acetone is added to a solution of (5-methyl-1,3-dioxol-2-on-4-yl)methyl bromide (0.772 g, 4 mmoles) in 10 ml of acetone. After stirring 0.5 hour, the reaction is concentrated to an oil, dissolved in $CHCl_3$ and filtered through 30 g silica gel with $CHCl_3$ eluant. The eluate is concentrated to yield title product.

EXAMPLE F16

(5-Methyl-1,3-dioxol-2-on-4-yl)methyl 6-alpha-(Glycyloxymethyl)penicillanate 1,1-Dioxide p-Toluenesulfonate Title product of the preceding Example (0.38 g, 0.80 mmole) is dissolved in 20 ml of water saturated ethyl acetate. p-Toluenesulfonic acid monohydrate (0.15 g, 0.80 mmole) in 10 ml ethyl acetate is added dropwise over 5 minutes. After stirring 0.5 hour under $N_2$, the mixture is concentrated to yield title product.

EXAMPLE F17

1H-Isobenzofuran-3-on-1-yl 6-alpha-[N-(2-methoxycarbonyl-1-methylvinyl)-glycyloxymethyl]penicillanate 1,1-Dioxide Title product of Example F14 4.4 g, 7.1 mmoles) is dissolved in 50 ml acetone and mixed with 1H-isobenzofuran-3-on-1-yl bromide (3-bromophthalide; 1.52 g, 7.1 mmoles) in 20 ml acetone. After stirring 2 hours, the mixture is concentrated to yield instant title product.

EXAMPLE. F18

1H-Isobenzofuran-3-on-1-yl 6-alpha-(Clycyloxymethyl)penicillanate 1,1-Dioxide p-Toluenesulfonate By the procedure of Example F16, title product of the preceding Example is converted to present title product.

I claim:
1. A compound having the formula

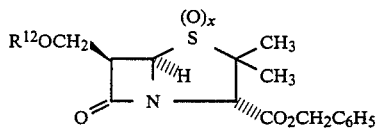
(V)

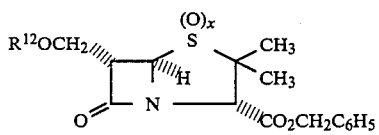
(VI)

wherein x is 0, 1 or 2; $R^{12}$ is

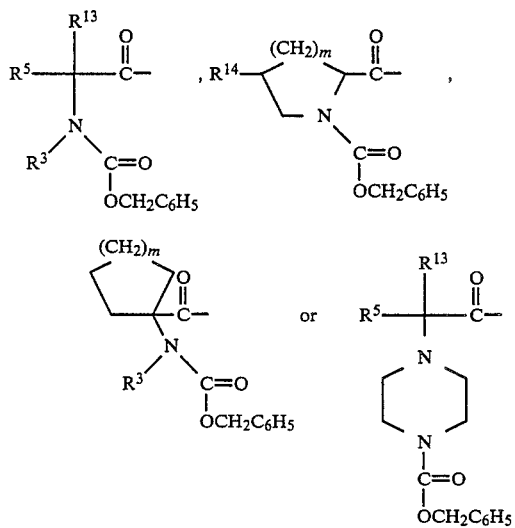

$R^3$ and $R^5$ are each independently hydrogen or $(C_1-C_3)$ alkyl;
$R^{13}$ is hydrogen, $(C_1-C_6)$ alkyl, phenyl or benzyl; or one of said $(C_1-C_6)$ alkyl, phenyl or benzyl monosubstituted with

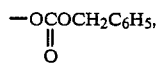

$-OR^3$, $-SR^8$, $-SO_2R^8$,

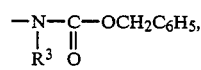

$-NR^8R^{15}$, $-NHCOR^3$, $-CONH_2$, $-COOCH_2C_6H_5$ or $-COOR^8$; $R^8$ and $R^{15}$ are each independently $(C_1-C_3)$alkyl $R^{14}$ is hydrogen, hydroxy,

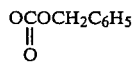

or $-OCOR^3$; and m is 0, 1 or 2.

2. A compound of claim 1 of the formula (V).
3. A compound of claim 1 of the formula (VI).
4. A compound of claim 1 wherein x is 0.
5. A compound of claim 1 wherein x is 1.
6. A compound of claim 1 wherein x is 2.
7. A compound of claim 1 wherein $R^{12}$ is

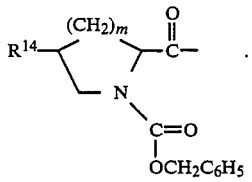

8. A compound of claim 7 wherein X is 2 and $R^3$ and $R^5$ are hydrogen.
9. A compound of claim 8 wherein $R^{13}$ is hydrogen, methyl or 2-carbamoylethyl.
10. A compound of claim 8 having the formula (V).
11. A compound of claim 10 wherein $R^{12}$ is in the L-form and $R^{13}$ is hydroxymethyl, 4-(benzyloxycarbonylamino)butyl, 2-(methanesulfonyl)ethyl, benzyl, isopropyl or 1-hydroxyethyl.
12. The compound of claim 10 wherein $R^{13}$ is hydrogen.
13. A compound of claim 7 wherein X is 0.
14. A compound of claim 13 having the formula (V) wherein $R^{12}$ is in the L-form, $R^3$ and $R^5$ are each hydrogen and $R^{13}$ is methyl, hydroxymethyl, 2-carbamoylethyl, 4-(benzyloxycarbonylamino)butyl, 2-methylthioethyl, benzyl, isopropyl, 2-hydroxypropyl or hydrogen.
15. The compound of claim 13 having the formula (V) wherein $R^3$, $R^5$ and $R^{13}$ are each hydrogen.
16. A compound of claim 1 wherein $R^{12}$ is

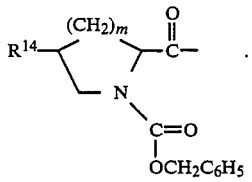

17. A compound of claim 16 wherein $R^{12}$ is in the L-form, X is 2, m is 1 and $R^{14}$ is hydrogen or trans-hydroxy.
18. The compound of claim 17 having the formula (V) wherein $R^{14}$ is hydrogen.
19. A compound of claim 16 wherein $R^{12}$ is in the L-form, X is 0, m is 1 and $R^{14}$ is hydrogen or trans-hydroxy.
20. The compound of claim 19 having the formula (V) wherein $R^{14}$ is hydrogen.

* * * * *